(12) United States Patent
Van Wie et al.

(10) Patent No.: US 6,544,162 B1
(45) Date of Patent: Apr. 8, 2003

(54) SEMI-CONTINUOUS, SMALL VOLUME CENTRIFUGAL BLOOD SEPARATOR AND METHOD OF USING THEREFOR

(75) Inventors: Bernard Van Wie, Pullman, WA (US); Trevan R. Landin, Vancouver, WA (US); Bruce N. Weyrauch, Otis Orchards, WA (US)

(73) Assignees: Washington State University Research Foundation, Pullman, WA (US); DevTec Inc., Spokane, WA (US)

( * ) Notice: Subject to any disclaimer, the term of this patent is extended or adjusted under 35 U.S.C. 154(b) by 0 days.

(21) Appl. No.: 09/403,475
(22) PCT Filed: Apr. 24, 1998
(86) PCT No.: PCT/US98/08228
§ 371 (c)(1),
(2), (4) Date: Feb. 8, 2000
(87) PCT Pub. No.: WO98/48938
PCT Pub. Date: Nov. 5, 1998

Related U.S. Application Data

(60) Provisional application No. 60/044,947, filed on Apr. 25, 1997, now abandoned.

(51) Int. Cl.[7] .......................... B01D 21/26; B04B 7/08; B04B 11/00
(52) U.S. Cl. ........................ 494/37; 494/35; 494/43; 494/83

(58) Field of Search ................ 210/782, 787, 210/789; 494/43, 35, 36, 37, 83; 422/72; 436/45

(56) References Cited

U.S. PATENT DOCUMENTS

| 347,702 | A | * | 8/1886 | Evans | |
| 4,378,906 | A | * | 4/1983 | Epper et al. | 494/54 |
| 4,386,730 | A | * | 6/1983 | Mulzet | 494/81 |
| 5,472,602 | A | * | 12/1995 | Feller et al. | 210/370 |

* cited by examiner

*Primary Examiner*—John Kim
(74) *Attorney, Agent, or Firm*—Wells St. John P.S.

(57) ABSTRACT

A centrifugal blood separator for separating whole blood into at least two blood fractions such as a plasma fraction and a blood cell fraction is disclosed. The blood separator has a centrifuge vessel with a separation chamber having at least two sections with different diametric sizes. The large diameter section collects the heavier blood cell fraction during centrifugation. The smaller diameter section collects the lighter plasma fraction. Fluid communication subassemblies preferably have a feed conduit, a product or an outflow conduit and a vent which are mounted in a non-rotatable part and positioned in an extending or extendible manner into the separation chamber to allow blood fractions to be removed while the centrifuge vessel is rotating or after rotation has stopped depending upon specifics of the particular embodiment.

40 Claims, 17 Drawing Sheets

SEMI-CONTINUOUS, SMALL VOLUME CENTRIFUGAL BLOOD SEPARATOR AND METHOD OF USING THEREFOR

REFERENCE TO RELATED APPLICATIONS

This is a national stage application based upon International Application Ser. No. PCT/US98/08228, filed Apr. 24, 1998, which claimed priority upon U.S. Provisional Patent Application Ser. No. 60/044,947, filed Apr. 25, 1997 (now abandoned).

FIELD OF THE INVENTION

The field of this invention is small volume centrifugal blood separators used to produce one or more fractions from whole blood, the fractions of whole blood being used for purposes such as analysis of the blood fraction or fractions for health diagnostics and other purposes.

BACKGROUND

It is frequently desirable in medical diagnostics and medical research to obtain information which indicates the blood chemistry of a patient or research subject. Blood chemistry is often the foremost or a very important variable which must be tracked to enable the physician or researcher added information or understanding to fully assess the situation at hand.

There also exists a need for more cost effective clinical blood analyzers that still meet stringent proficiency requirements imposed by medical practice and the Clinical Improvement Act implemented by the U.S. Congress in 1988. The proficiency requirements place added emphasis on obtaining reliable blood chemistry analyses with reduced blood sample volumes.

Another factor relevant to blood separation and analysis is the decreasing number of certified medical technologists over the past ten years. This coupled with growing concerns about handling and disposal of biomedical samples and waste has made blood separation and analysis an increasingly difficult problem for the medical services industry and medical research.

To help address these issues, it is desirable that clinical analyzers be less expensive to enable a larger number of blood separation and analysis equipment to be employed. Lower instrument prices, more efficient operation and lower costs per test are all targets of improved blood separation techniques. It is also desirable to provide blood separation equipment which has simplified operation so that personnel of more limited skill can perform the required operations associated with separation and analysis of blood. It is also desirable to better enable critical care monitoring through use of blood separation and analysis equipment which is compact, portable yet maintaining the high degree of reliability important in testing small amounts of whole blood. It is further desirable to provide blood -separation equipment which minimizes or reduces health risks by providing contained waste systems and by eliminating, where possible, contact of the operator with the specimen.

BRIEF DESCRIPTION OF THE DRAWINGS

Preferred embodiments of the invention are described below with reference to the following accompanying drawings.

BEST MODES FOR CARRYING OUT THE INVENTION

Separator Generally

Figure 1:
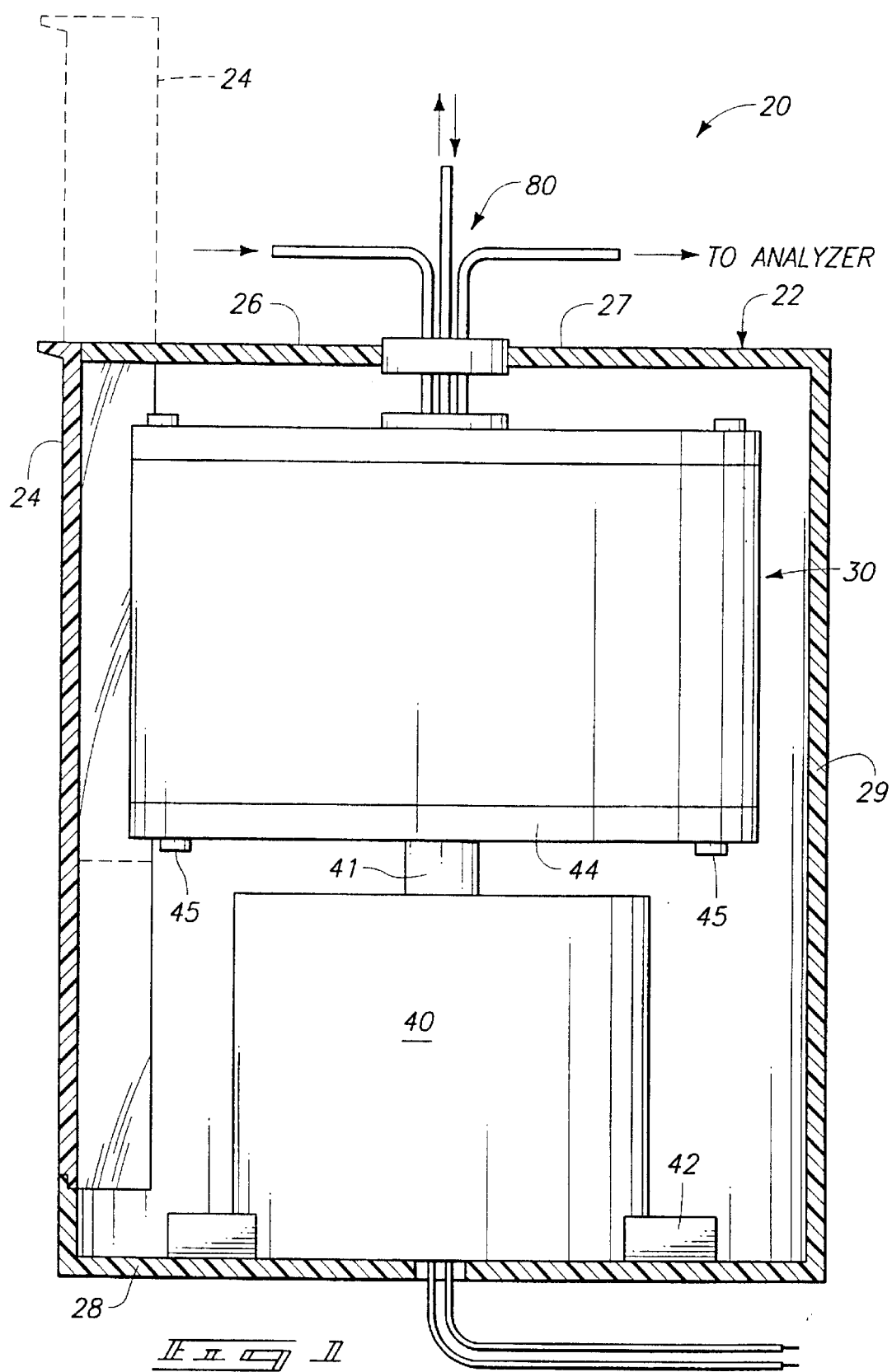
FIG. 1 is a side view of a preferred blood separator according to this invention. Outer housing portions of the blood separator are shown removed and in sectional presentation.

FIG. 1 shows a preferred blood separator 20 according to the invention. Blood separator 20 includes an -outer housing 22 which serves as a shielding structure which encloses a centrifuge vessel 30. The housing has a top wall 27, bottom wall 28, and cylindrical side wall 29.

The housing 22 preferably has a front access door or panel 24 which is slidably mounted relative to stationary portions 26 of the housing 22. The access door 24 forms a part of the sidewall when in the closed position. FIG. 1 also shows the access door 24 in a partially raised condition in phantom lines to show how the housing is opened to allow access to the centrifuge vessel and other components within the housing. The access door can be totally removed by sliding it upwardly and out of engaged relationship with the stationary portions of the housing.

The separator 20 also includes a drive 40 which is described in greater detail below. The separator further includes fluid communication fitting 80 which allow fluids to be supplied or withdrawn from the inside of centrifuge vessel 30. The details of the preferred features are further explained below.

Separator Drive

Separator 20 also includes a drive motor 40 which is securely mounted to the housing 22 at mounts 42 which can be mounting blocks with threaded fasteners (not shown) or other suitable mounting means. The drive motor 40 is advantageously an electrical motor with an output shaft 41. The drive motor is preferably provided with speed control circuitry (not shown) having the capability to allow different rotational speeds to be used. The electric motor is preferably controlled by a variable speed load-sensitive controller which will help maintain a predetermined rotational speed. The motor and control circuitry are conventional and can be selected from a wide variety of suitable alternatives. Typical operating speeds are expected to be in the range of 500–10,000 revolutions per minute (rpm), although other operating regimes are not disqualified by the teachings of this invention.

The output shaft 41 of the drive motor is connected to a drive mounting plate 44. The centrifuge vessel 30 is mounted in a detachable manner to the drive mounting plate 44 using centrifuge vessel mounting fasteners 45. This arrangement allows the separator to be fitted with several different types of centrifuge vessels which may have varying advantages depending upon the particular blood separation processes being performed.

First Embodiment Centrifuge Vessel

Figure 2:
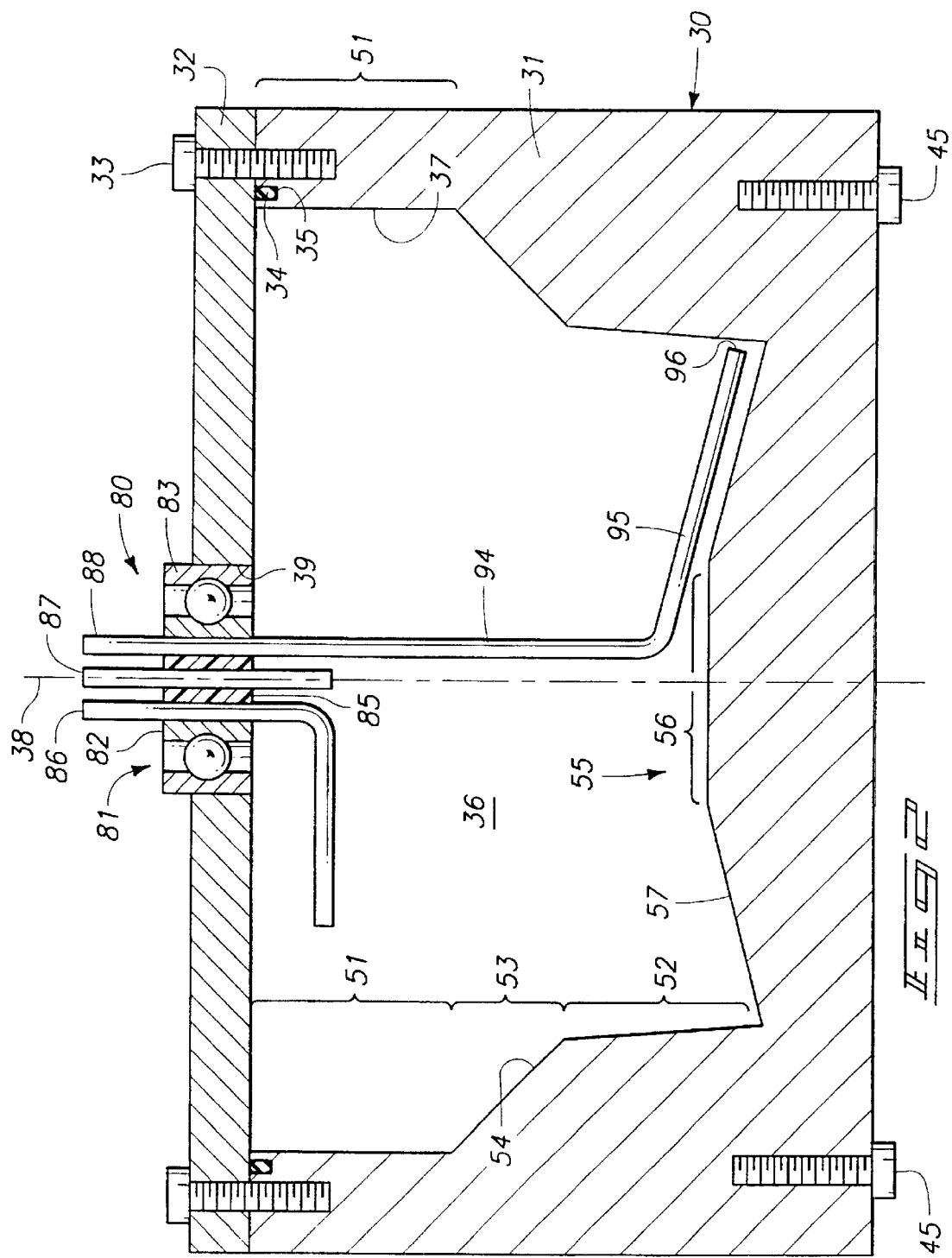
FIG. 2 is an enlarged, side sectional view of the centrifuge vessel shown as part of the separator illustrated in FIG. 1. The centrifuge vessel is shown in isolation from other parts of the blood separator.

FIG. 2 shows a preferred construction for centrifuge vessel 30. Centrifuge vessel 30 includes a main vessel part 31 and a detachable vessel cover 32. Cover 32 is secured by cover mounting fasteners 33 which extend through the mounting apertures formed in the cover and are received in threaded receptacles formed in the main vessel part 31.

Vessel 30 also advantageously includes a peripheral cover seal 34. Seal 34 is preferably included and positioned within a cover seal annular receptacle 35 formed in upper surfaces of the main vessel part 31. This construction forms a centrifuge vessel 30 which has a substantially enclosed and sealed separation chamber 36 enclosed therewithin.

The separation chamber 36 is specially shaped to serve the centrifugal separation functions for which it is intended. The separation chamber includes side walls 37 which have a first section 51 which has a diametral size which is larger than a second section 52. The first and second sections 51 and 52 are advantageously connected by a third section 53 which has a transitional slope 54. The first, second and third sections 51–53 are advantageously arranged in spaced axial positions along the rotational axis 38. During operation, the sections 51–53 facilitate separation of different fractions of blood based upon different settlement densities under the forces of centrifugal action. Additional explanation is provided below concerning such operation.

The separation chamber 36 is also partly defined by the lower surface or wall 55 of the chamber. As shown the lower or end wall 55 has a central section 56 which is flat or appropriately domed. The outer annular section 57 is sloped to facilitate collection of any fluids toward the outer periphery of the bottom or lower end wall 55. This facilitates removal of fluid contents from the separation chamber, such as via outflow tube 88 which will be further discussed below. Other alternative end or bottom wall configurations are also possible, such as some of the alternative constructions detailed below.

The centrifuge vessel 30 also includes cover 32 which is advantageously provided with a fluid communication subassembly 80. Fluid communication subassembly 80 advantageously includes a bearing 81 or other suitable rotational fixture at a central location aligned to rotate with the centrifuge rotational axis 38. Bearing 81 can be of various types and constructions so as to support the inner race 82 in free or relatively free rotation relative to the outer race 83.

Outer race 83 is connected to cover 32 and rotates therewith. The outer race can be connected to the cover in a variety of constructions, such as a press fit within a central aperture 39 formed in cover 32.

The inner race 82 supports a conduit mounting plug 85 which can be fitted with one or more openings through which the fluid communication conduits 86, 87 and 88 are extended. Fluid communication conduit 86 is advantageously provided in the form of a supply or feed conduit which has a lateral leg extending laterally within the separation chamber 36. The lateral leg is designed to feed an inflowing whole blood sample into the first section 51, such as may be desired if as the centrifuge vessel 30 is rotating.

The fluid communication subassembly 80 also preferably includes a vent tube or conduit 88. Vent tube 88 can be connected to communicate outside of the housing 22, as shown in FIG. 1, or can merely vent within the housing. The vent tube allows for venting so that fluids can be easily supplied to or withdrawn from the separation chamber 36 without differential pressures impeding such flows.

The fluid communication subassembly 80 also preferably includes a product or outflow conduit 88 which is specially configured to add in removal of blood fraction during operation. The product outflow conduit has an axial extension portion 94 and a lateral depending leg 95 (see FIG. 2). This shape positions the suction port 96 of the product conduit in a lower outside position which enables most of the contents of the separation chamber to be withdrawn by evacuation through conduit 88.

Exemplary Operation of First Embodiment

Separator 20 is intended to separate small volumes of whole blood, such as samples ranging from 1.0–1.2 cubic centimeters (cc). It produces two blood fractions from the whole blood. One fraction is the resulting plasma which is free or substantially free of red blood cells (RBC), white blood cells (WBC), and platelets. The resulting plasma can be supplied to a flow injection analyzer (FIA) (not shown). The flow injection analyzer or other suitable analyzer will then be used to perform various blood chemistry analyses. Exemplary analyses include the eight most common clinical tests performed upon blood plasma, well known in the art, or other alternative tests as the medical professional or researcher may desire. The particular test employed is not essential and in general does not dictate a particular configuration for the blood separator, although some separator designs will be of greater advantage for a particular test or battery of tests being run on the outflowing blood fraction product or products being produced by the separator.

One exemplary analysis system is connected to product line 88 and receives fluids downstream of the blood separator 20 via product line 88. Such an analytical system receives samples at approximately 1 minute intervals. In such an analyzer system the samples are fed to a microfluidic FIA analyzer that splits the plasma or serum into eight sequential sample/reagent pairs separated by air bubbles. All eight pairs will pass by a photodiode array with the data being stored and analyzed via computer interface. Many other types and forms of analyzers can alternatively be used.

Separator 20 is designed to separate the cellular components from whole blood. The separator employs a rotating chamber that contains various reservoirs which aid in the separation. The preferred constructions contain all features needed to supply and remove the blood supply and resulting fractions within the separation chamber while the device is spinning, if desired. In the embodiment shown in FIGS. 1–5, the heavy components, for example blood cells, are removed once the centrifuge vessel has stopped rotation. This can be done manually by opening the centrifuge vessel, or more preferably by using the product conduit 88 as explained below.

The centrifuge vessel and motor are housed within housing 22 which also functions as a protective blast shield which protects the operator from harm if something should break during normal operation. The speed of the centrifuge vessel 22 is can be set with the aid of a strobe light (not shown) which can be either separate from or an integrated part of the blood separator itself.

Figure 3:
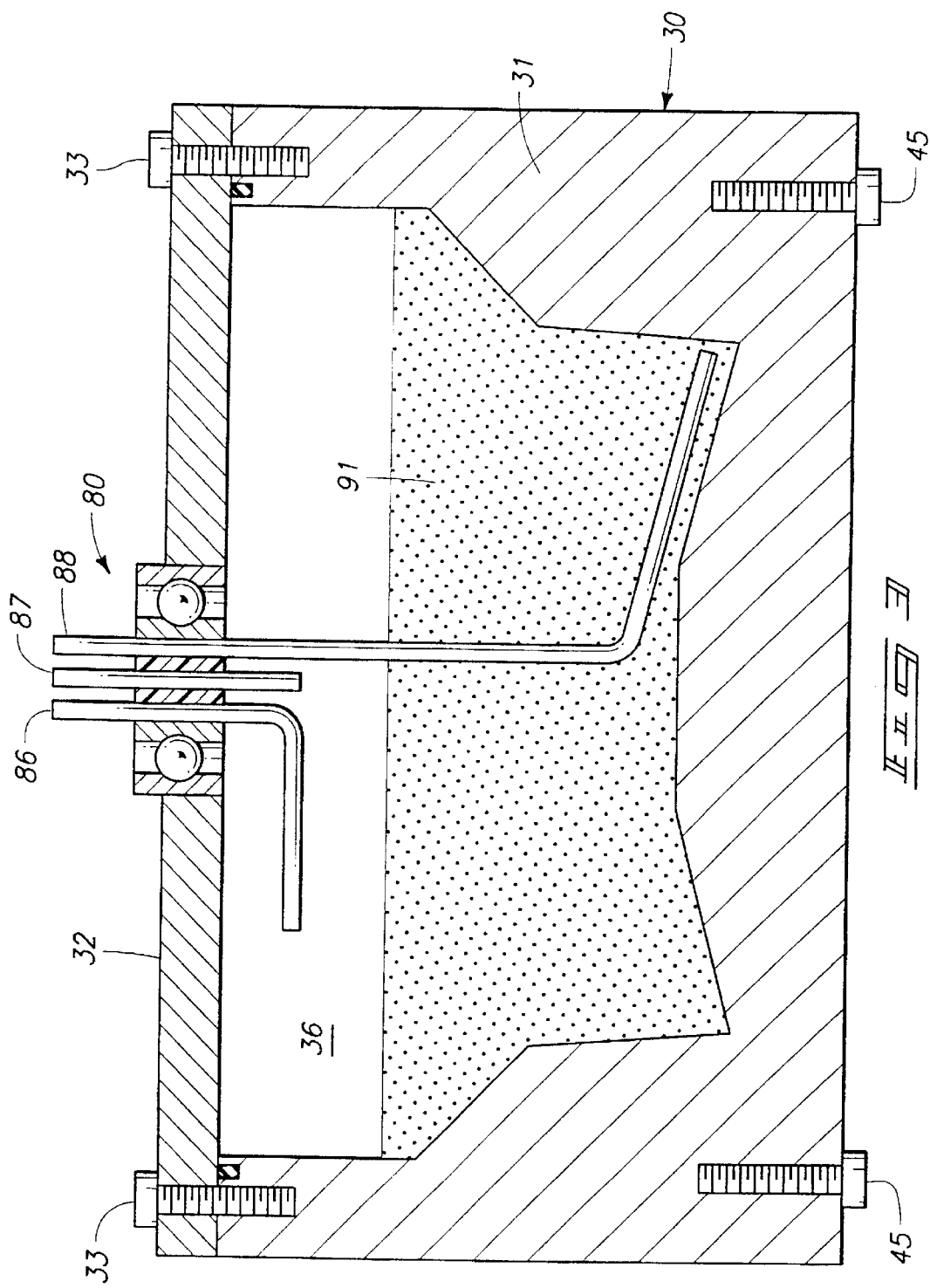
FIG. 3 is a view similar to FIG. 2 with the separation chamber of the centrifuge vessel supplied with a charge of whole blood ready for separation.

FIG. 3 shows the separation chamber 36 provided with a charge of whole blood 91, which was fed in through feed conduit 86 with the centrifuge vessel 30 stationary. Alternatively, the charge of whole blood can be fed through infeed conduit 86 while the centrifuge vessel is rotating.

Figure 4:
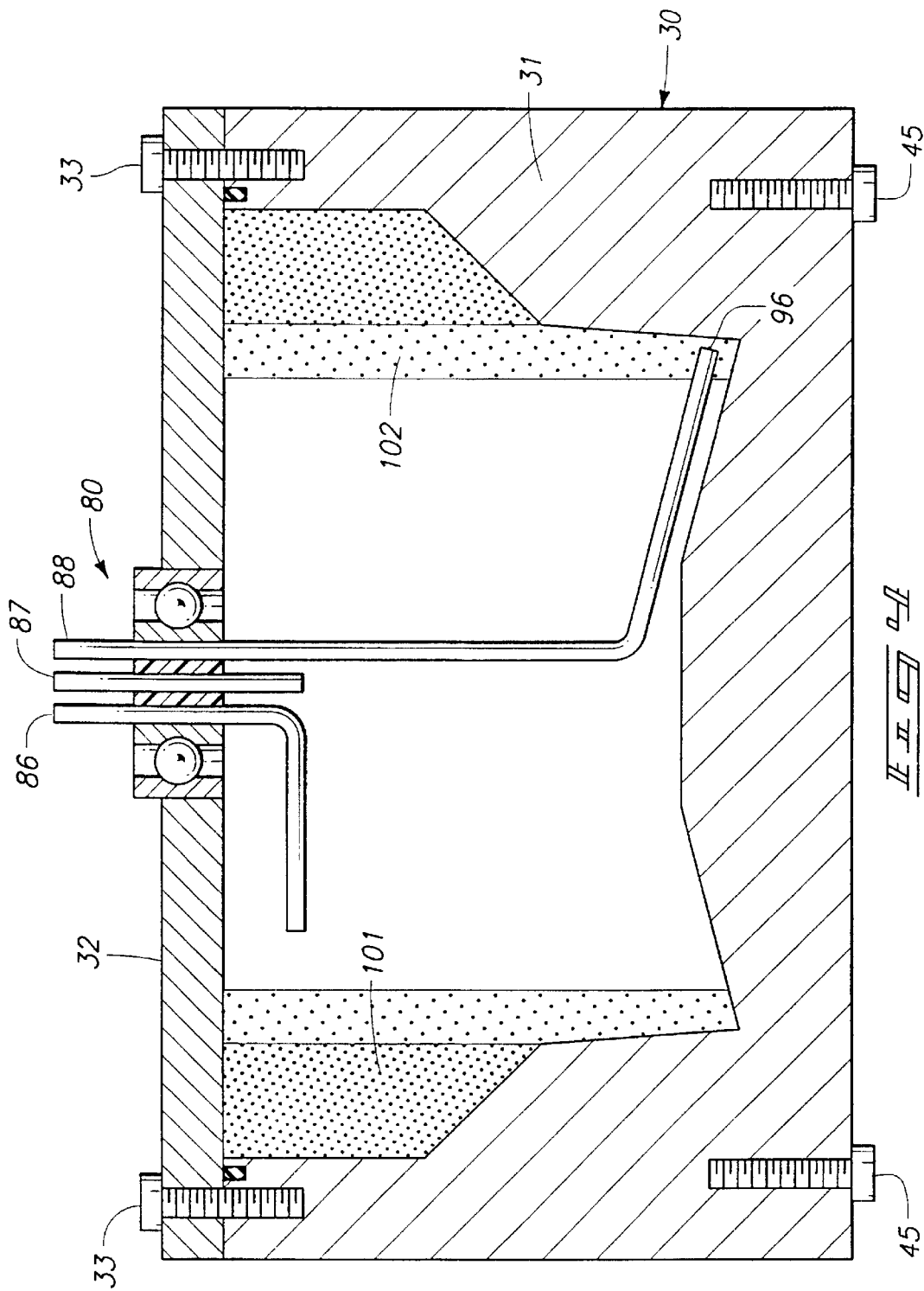
FIG. 4 is a sectional view similar to FIGS. 2 and 3 with the centrifuge vessel shown in operation. During operation the sample of whole blood is being separated into two fractions which are illustrated by differing dot concentrations.
Figure 5:
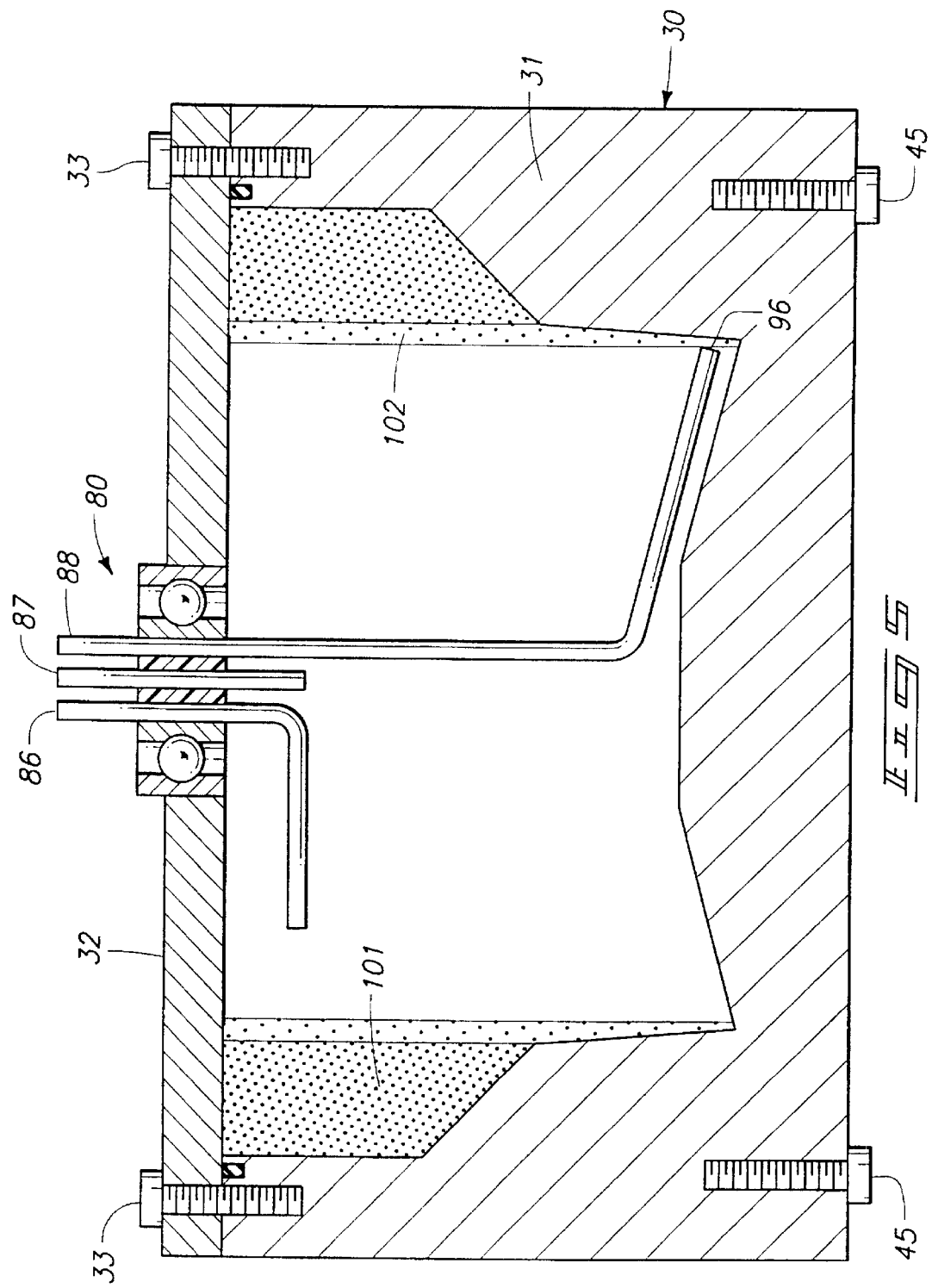
FIG. 5 is a sectional view similar to FIG. 4 which shows operation after a portion of the lighter blood fraction has been withdrawn from the separation chamber via an outflow or product conduit.
Figure 6:
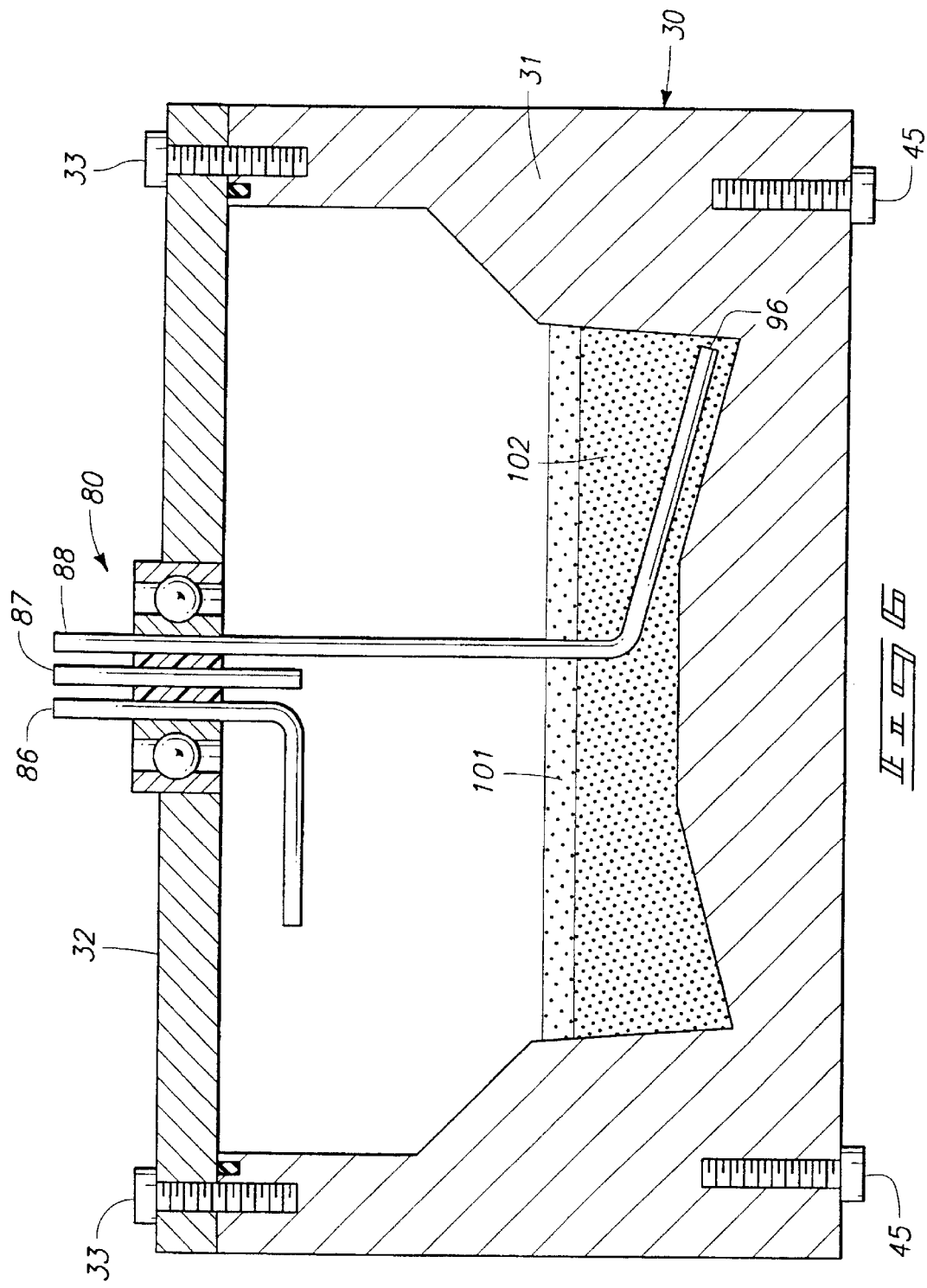
FIG. 6 is a side sectional view similar to FIG. 5 after rotation and withdrawal of serum and prior to removal of the heavier blood fraction.

FIG. 4 shows the centrifuge vessel 30 in operation with the vessel rotating at a sufficient rotational speed to force the fluid contents of chamber 36 against the side wall. FIG. 4 shows the blood sample separated into two different fractions. The heavier fraction 101 is forced into the first section 51 and such fills the first section and transition section 53. The lighter fraction 102 represents the blood plasma and such is inwardly of the heavier fraction. The geometry and size of the separation chamber is made appropriate to routinely cause the plasma to be present so that at least a portion of the plasma can be withdrawn by suction applied to the suction port 96 at the distal end of the product conduit 88. The size and geometry of the chamber 36 is also designed so that withdrawal of the lighter fraction by conduit 88 does not lead to withdrawal of the heavier fraction 102 due to the dam formed by the transition or third section 53. This allows the lighter fraction to be withdrawn during rotation as is illustrated by FIG. 5. The heavier fraction is thereafter withdrawn after rotation is slowed or totally stopped so that the primarily heavy fraction settles in the separation chamber, as is shown in FIG. 6. The bottom wall configuration aids in allowing the removal of both fractions by positioning the suction port 96 adjacent to a well or lower position when in both a rotational mode of operation and a nonrotational mode of operation.

Example Procedure

In order to investigate the separation characteristics of centrifugal blood separator 20 we used whole pig blood for our preliminary experiments. Pig blood was chosen because of its similarities with human blood. The cellular composition of pig blood is as follows: 42–45% hematocrit (HCT), and 58–55% plasma. White blood cells and platelets make up less than 1% of the total blood volume.

The separator 20 was operated using the following procedure. The desired rotational speed was set using a strobe light (not shown) which was beamed onto the rotating centrifuge chamber through the transparent housing 22. The rotational speed was checked periodically during the separation procedure to ensure a constant operating speed.

The whole blood sample was injected into the separation chamber via feed conduit 86 using either a peristaltic pump (not shown) or a syringe (not shown). For this specific separation chamber size and configuration, the desired blood charge was limited in the range between 1.0–1.2 cc. This was a relatively small volume of blood yet was found sufficient to provide blood fractions which could be successfully analyzed. It is also contemplated that even smaller volumes, such as in the range of 0.2–0.5 cc will be used with correspondingly sized separation chambers.

The separator was allowed to rotate and otherwise operate for the desired time, typically in the range between 1 to 2 minutes. The amount of time used depended upon the speed of the rotor (centrifuge vessel and motor moving parts), and the degree of separation desired. Typical rotational speeds will depend upon the size and geometry of the separation chamber 36. Routinely, the operational speeds will be in the range of 500–10,000 rpm, more preferably in the approximate range of 1000–5,000 rpm.

Visual examination to determine a suitable separation time is also permitted if the degree of separation was not critical to the experimental analysis being conducted. Visual examination is accomplished by observing the lower or second section 52, and then removing the plasma when a clear solution is observed in that section. This viewing is possible when the vessel is made with transparent materials, such as a high strength plastic, such as polycarbonate or acrylic.

The resulting plasma usually measured in the range of approximately 0.150–0.350 cc. The removed plasma was collected in an appropriate storage vessel (not shown) and then suitably stored for future analysis. Alternatively, the resulting blood fraction can be immediately analyzed according to a large variety of plasma or other blood fraction analytical tests.

After one or more lighter fractions have been removed as discussed above with rotation assisting in the segregation of the blood fractions, then one or more heavier blood fractions are then removed from the separation chamber. This is most preferably accomplished with the centrifuge vessel in a stationary or nonrotating condition. FIG. 6 illustrates the redistribution of the heavier cellular components which drain toward the bottom of the separation chamber. Under centrifugation these heavier components have collected in the upper reservoir or first section. After they drain downwardly, then they can be removed using a suitable means, such as with either a peristaltic pump or a syringe.

After the heavier fraction has been removed via the product conduit 88, then some residual materials will typically remain. These residuals must be removed if the chamber is to be reused for separation of another blood sample. This is advantageously accomplished using several rinsing cycles, such as approximately 5 to 8 rinse cycles. The rinse cycles can be performed using various fluids, but are suitably performed using a 0.15 M NaCl saline solution. The separation chamber is filled with roughly 1.0 cc of such saline solution and then turned on for a fraction of one second or other suitable time period. This is done to wash the walls within the separation chamber and to flush the fluid conduits 86 and 88 with the entering and withdrawn fluids. The resulting rinse solution is then removed and the procedure is then repeated until a clear solution is observed within the separation chamber and with regard to the withdrawn rinse solution. These rinsing operations ensure that all or a sufficiently large portion of any residual cellular waste has been removed from the separation chamber. The separator is then ready for another separation.

EXAMPLE 1

Qualitative and Quantitative Results

The next step is to outline the qualitative data obtained during the initial separation experiments. The table below illustrates the visual characteristics that were observed during normal operation of the device.

TABLE 1

QUALITATIVE RESULTS

|  | Clarity | Tint | Foaming | Separation Time |
|---|---|---|---|---|
| Control Plasma | Translucent | Yellow | None | 5 min. |
| 2000 | Translucent | Yellow | None | 4 min. |
| 3000 | Reddish | Yellow | Slight | 2 min. |
| 4000 | Reddish | Yellow | Moderate | 1 min. |
| 5000 | Reddish | Yellow | Severe | 0.50 min. |

Clarity: This is an indication of whether cells or platelets, etc., exist in suspension; a reddish translucence indicates that RBC's are present, while translucence indicates that platelets and WBC's are in suspension.

Tint: This is an indication of cellular damage; a pink transparent tint indicates that RBC hemolysis has occurred.

Foaming: An indication of possible protein damage.

Separation Time: The time it takes to visually observe a definite plasma/cell interface.

Table 1 indicates that separation can be determined visually. The heavy cellular portion of the blood can be seen collecting in the upper section of the separation chamber, while the plasma collects selectively in the lower section. When the color becomes translucent in the lower section, then the separation is virtually complete.

Table 2 indicates the platelet, WBC, RBC, HCT, and hemoglobin composition of several different samples. Experiments were performed at 2000, 3000, 4000, and 5000 rpm. The resulting plasma was removed from separator 20 after each experiment and then tested for hemoglobin content using a traditional blood chemistry analyzer, and for cellular components using a traditional cell counter. A whole blood sample was analyzed in order to determine the concentrations of specific cellular components that are to be removed. The control was established using a standard bench centrifuge to perform the separation.

Figure 7:
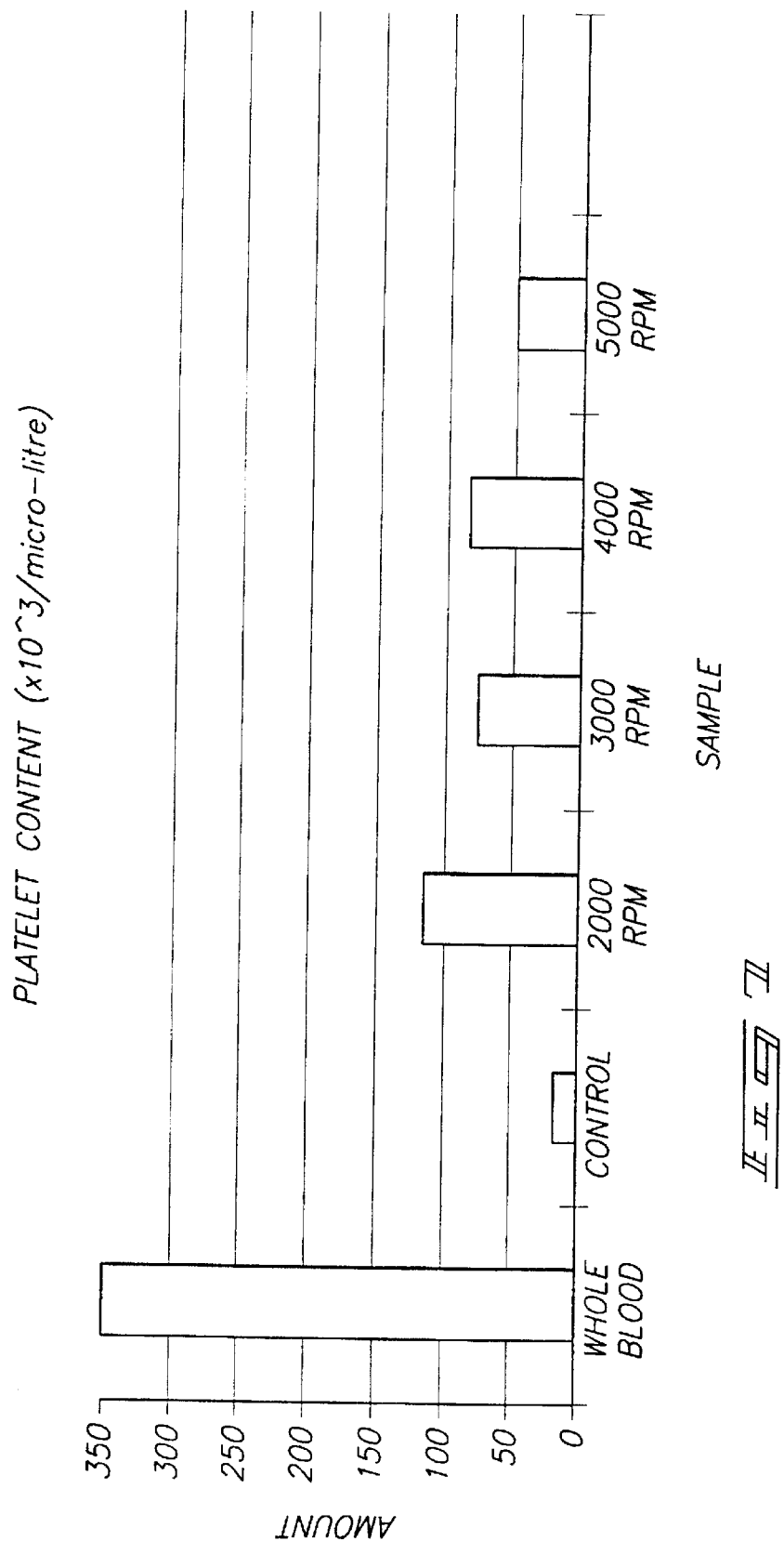
FIG. 7 is a graph showing exemplary results obtained using the centrifugal separator of FIG. 1.

FIG. 7 indicates the platelet content for various samples. The small amount of platelets present in the control is noteworthy.

The platelet content of the control sample, 17,000 platelets/microliter, is approximately 67% less than the platelet content observed using separator 20 operated at 5000 rpm. Since the settling velocity of platelets is the lowest of all cellular components within the blood, we assume that the platelets are the last item to be removed from the plasma. Therefore, platelet concentration could be used as an indicator to determine the overall separation of the whole blood.

Specific indicators which can be used to determine the degree of separation are outlined in Table 2.

TABLE 2

SEPARATION INDICATORS

| Sample Type | HCT | RBC's/ micro-1 (x10^6) | WBC's/ micro-1 | Hb g/dec-1 |
|---|---|---|---|---|
| Whole Blood | 41% | 7.50 | 13,700 | 13.4 |
| Control Plasma | 0 | 0.01 | 200 | 0 |
| 2000 | 0 | 0.04 | 500 | 0 |
| 3000 | 0 | 0.04 | 400 | 0 |
| 4000 | 0 | 0.04 | 400 | 0 |
| 5000 | 0 | 0.06 | 300 | 0 |

Table 2 indicates separation indicators which may be used to determine overall blood separation. The HCT levels for all samples, but whole blood, are zero as well as the hemoglobin (Hb) levels. Therefore these items may not be sufficient to determine the degree of separation. The RBC and WBC content may be better indicators for his determination. The WBC content is lowest in the control plasma, followed by the trial at 5000 rpm. This would indicate that the WBC's are the second to last item to be removed from the sample. This is evident when analyzing the settling velocity of the WBC's in comparison to platelets and the RBC's.

The blood separator 20 was found to be successful in separating plasma from whole blood. It was observed that separation time increases with decreasing rotational speed. The degree of separation can be roughly determined by visual inspection of the solution within the device. In order to separate the sample within a one minute time interval, speeds in excess of 4000 rpm must be applied. A baseline, or noise level, is best determined in order to better determine where the operating range of the separator lies. The best case scenario would place this operating range at 5000 rpm. At this operating speed the separator will deliver a product which most closely resembles the plasma produced using a standard bench centrifuge.

The following observations may further be appropriate but are as yet not confirmed. Rotational speeds in excess of 5000 rpm may be in order to achieve the degree of separation which is achieved using standard bench centrifugation. A longer separation time may be required, 1.5 or 2.0 min at 5000 rpm, in order to assure that virtually all platelets and WBC's are removed from the plasma. A removable pick-up tube may be desirable in order to assure that the proteins are not damaged during normal operation of the device. Further testing is in order to assess the actual damage, if any, of the proteins within the resulting plasma.

Second Embodiment Centrifuge Vessel

Figure 8:
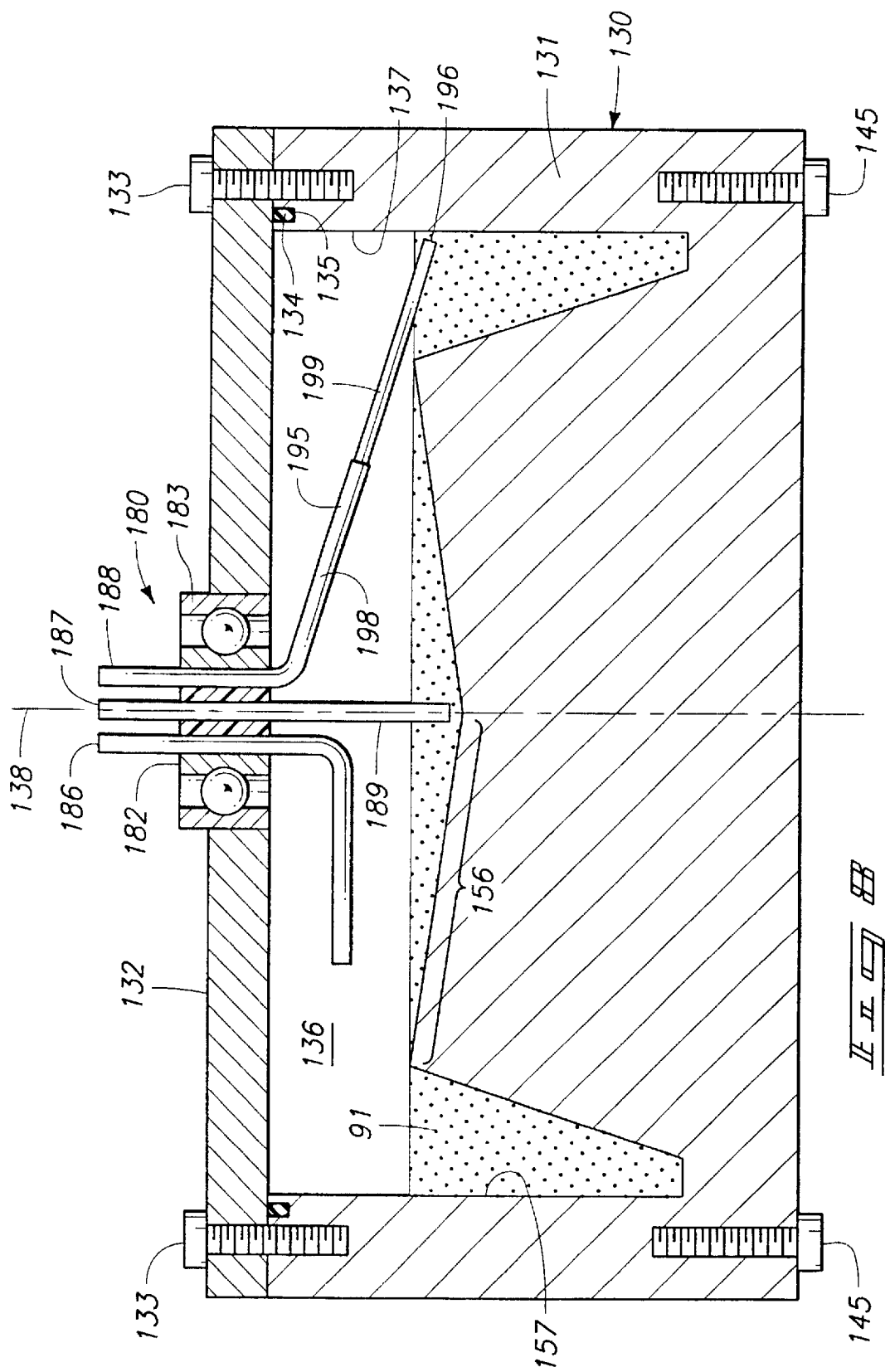
FIG. 8 is a side sectional view of a second embodiment centrifuge vessel according to the invention. The separation chamber is shown charged with a whole blood sample.

FIG. 8 shows a second embodiment centrifuge vessel 130 in accordance with the invention. The features of vessel 130 are similar to vessel 30 described in detail hereinabove. Reference numerals in FIG. 8 have been used which are the same as those used in FIGS. 2–6 with the addition of a "1" in the hundreds column. For example the vessel in FIG. 8 is 130 whereas the vessel in FIG. 2 is 30. Similar parts will not be described again for sake of brevity. The following discussion is directed to distinguishing features associated with centrifuge vessel 130 as compared to vessel 30.

The main vessel body 131 has a separation chamber 136 which is shaped differently from separation chamber 36. The side walls 137 of separation chamber 136 are substantially cylindrical. The bottom or end wall is convoluted and includes a central region 156 which is recessed to form a central receptacle. In the depiction of FIG. 8, the separation chamber has been charged with whole blood 91 which inundates the periphery of the central receptacle 156. The charge of whole blood also extends into and fills an annular trough 157 which extends around and encompasses the central island which defines upon its upper surface the central receptacle 156. Thus the separation chamber has a first section formed by trough 157 which has a greater diametral size than the more inward central receptacle 156.

FIG. 8 also shows that the centrifuge vessel is advantageously equipped with fluid communication conduits 186, 187 and 188. Feed conduit 186 is the same or very similar to conduit 86 described above. Alternatively, a blood sample can be supplied through conduit 187 and the conduit 186 can temporarily or regularly function as a vent. The conduit 187 can also have dual function by servicing as both a feed or supply conduit, and as a first product or outflow conduit during processing.

FIG. 8 also shows a second product or outflow conduit 188 which extends laterally at section 195. Conduit 188 has an outer sleeve portion 198 which supports an extendable part 199. The extendable part 199 extends into the annular trough 157 to allow removal of the heavy fraction either during or after rotation. The bottom or distal end of the conduit 188 has an outflow or suction port 196 through which a blood fraction or fractions can be withdrawn or otherwise flow.

Figure 9:
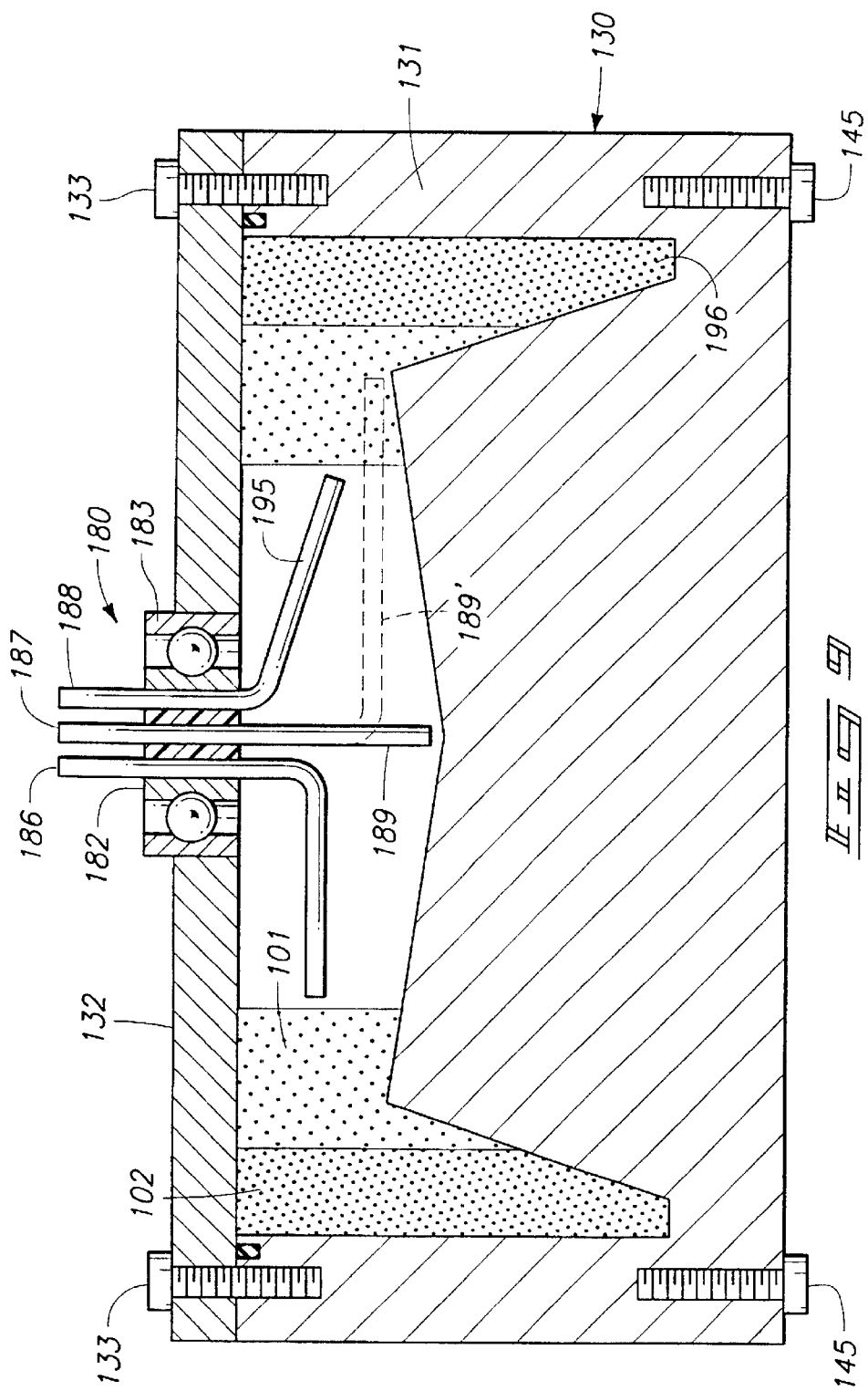
FIG. 9 is a side sectional view similar to FIG. 8 after the separation process has been performed and in anticipation of withdrawal of blood fractions from the separation chamber.

FIG. 9 shows centrifuge vessel 130 during centrifugal operation. The centrifugal forces cause the whole blood to spin against the side wall and into a first or lighter fraction layer 101 and a second or heavier fraction layer 102. The operation of centrifuge vessel 130 can be performed in two different modes of operation which will now be explained in greater detail.

In a first mode of operation the lighter fraction 101 is withdrawn from the separation chamber 136 while rotation continues. This is best accomplished using a modified or alternative first product conduit 189' which is shown in phantom and is extendable like part 199. In this alternative construction the first product outflow conduit extends laterally and ends in a distal suction opening which is within the lighter fraction layer 101. The plasma or other lighter fraction can thus be withdrawn on the fly without slowing or stopping rotation. This may be preferred in some applications.

Figure 10:
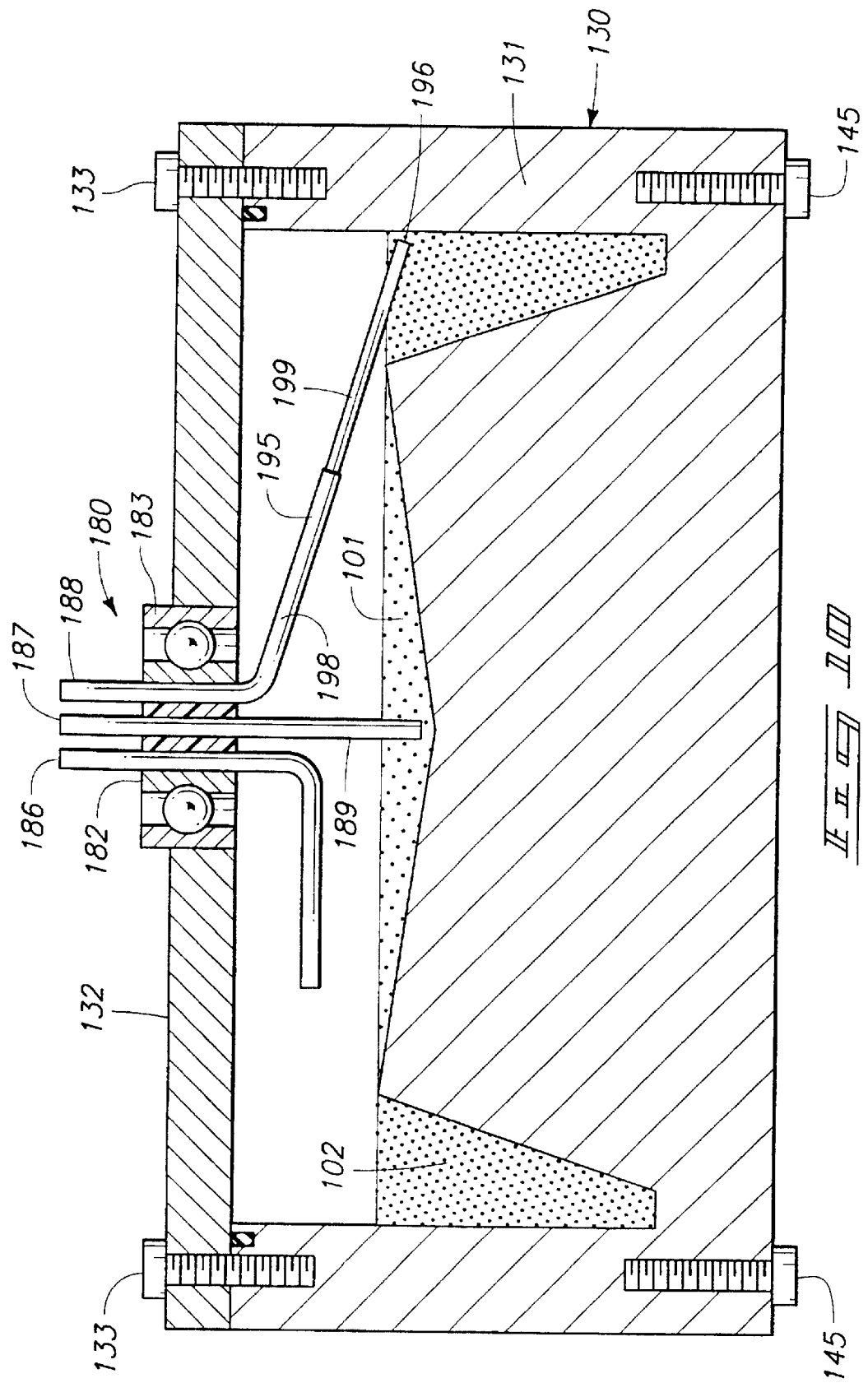
FIG. 10 is a side sectional view similar to FIG. 9 after separation has been performed and after rotation has been stopped. This view also shows the separation chamber prior to removal of blood fractions.

In the other alternative mode of operation and construction the first product outflow conduit 189 extends to lower reaches of the receptacle 156 as shown in FIG. 10. The suction port of conduit 189 thus is positioned in the lighter fraction 101 after centrifugation has been completed. Relatively precise total sample volume is needed in this last operational mode, or else the degree of separation is less demanding since some mixing may occur at the periphery during stoppage of the centrifuge vessel.

In either operational mode, the second product outflow conduit 188 is able to withdraw the heavier fraction 102 during either continued rotation or after the centrifuge has ceased rotation. The rotational product extraction is suggested by the extended position illustrated by FIG. 8 and the nonrotatable product extraction is illustrated by FIG. 10. It is also possible to have operational regimes which may be effectively a combination of the rotational and nonrotational extraction methods explained above to allow partial or total extraction of the first fraction during rotation or nonrotation, coupled with partial or total extraction of the second fraction during rotation or nonrotation.

Third Embodiment Centrifuge Vessel

Figure 11:
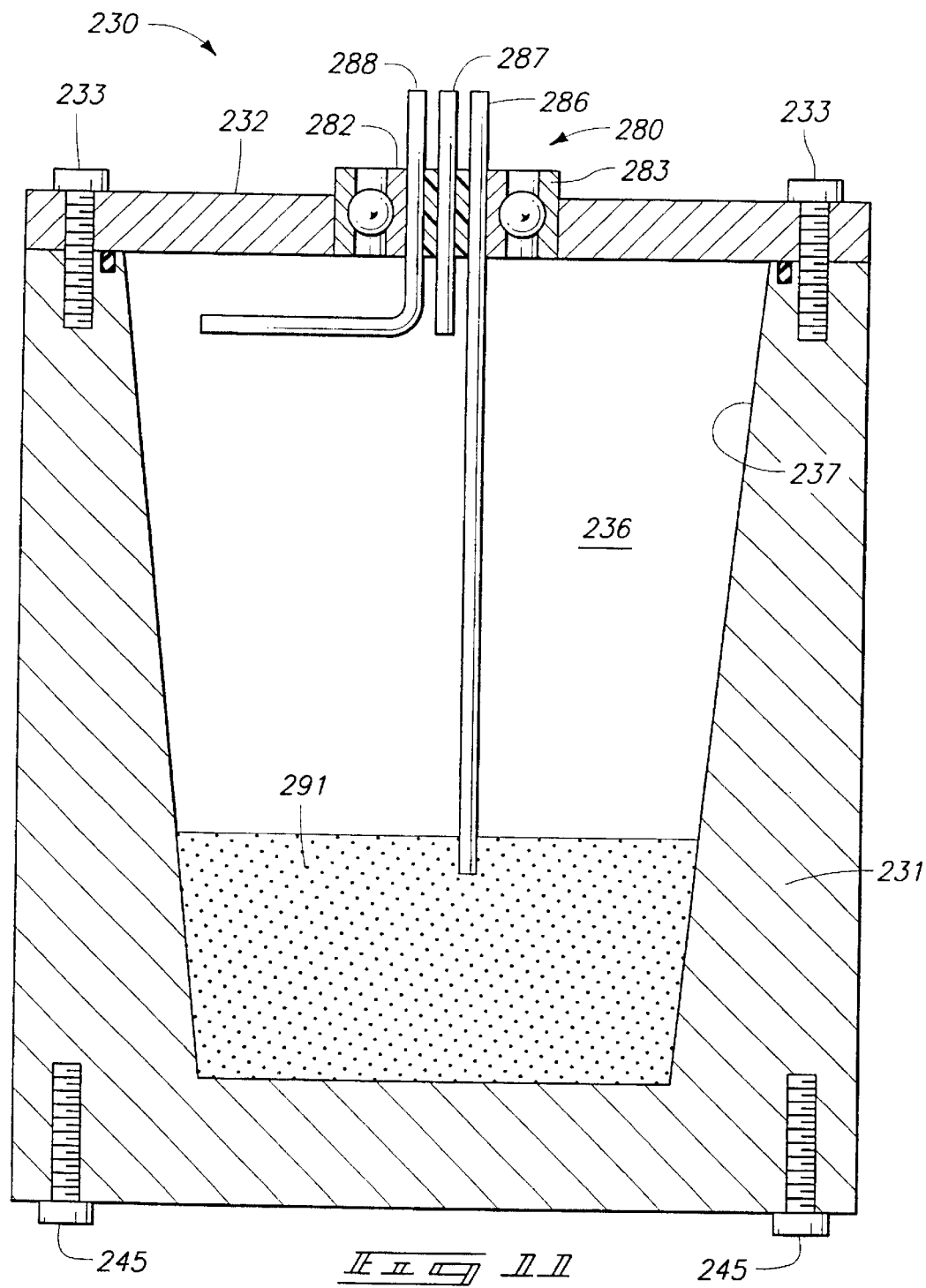
FIG. 11 is a side sectional view of a third embodiment of centrifuge vessel according to this invention. The centrifuge vessel is shown charged with a sample of whole blood.
Figure 12:
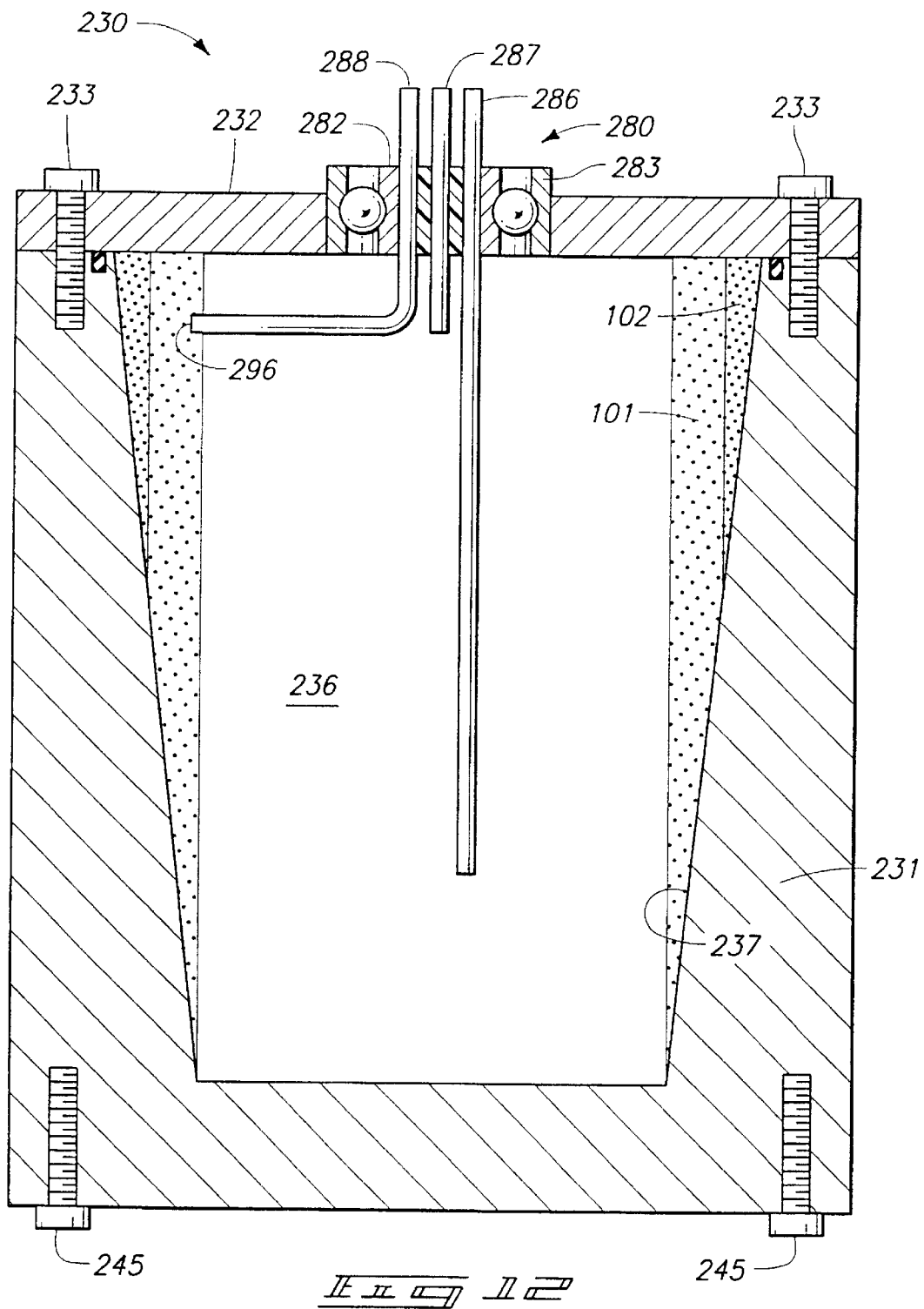
FIG. 12 is a sectional view similar to FIG. 11 with the centrifuge vessel in operation.

FIGS. 11 and 12 show a third embodiment of centrifuge vessel 230 according to another form of the current invention. The features of vessel 230 are similar to vessel 30 described in detail hereinabove. Reference numerals in FIG. 8 have been used which are the same as those used in FIGS. 2–6 with the addition of a "2" in the hundreds column. For example the vessel in FIG. 11 is 230 whereas the vessel in FIG. 2 is 30. Similar parts will not be described again for sake of brevity. The following discussion is directed to distinguishing features associated with centrifuge vessel 230 as compared to vessel 30 or vessel 130.

FIG. 11 shows that the centrifuge vessel 230 has a separation chamber 236 which is preferably formed with side walls 237 which converge downwardly. FIG. 11 shows a feed conduit 286 which extends downwardly near the central axis of the centrifuge vessel. A charge of whole blood 291 is shown installed within the separation chamber.

FIG. 12 shows the same centrifuge vessel 230 during operation and rotation. The whole blood sample has been spun and separated into a lighter fraction 101 and a heavier fraction 102. An outflow product tube 288 is provided with a suction port 296 which is positioned to be within the lighter fraction layer 101 during rotation. This allows the lighter fraction to be withdrawn during rotation. The exact positioning of port 296 will affect the amount of the lighter fraction which can be withdrawn. Portions of the heavier fraction are extracted using the feed tube 286 after rotation is ceased and the remains have settled into the bottom of the separation chamber in a fashion similar to that shown in FIG. 11. Other alternative conduit arrangements can also be used.

Fourth Embodiment Centrifuge Vessel

Figure 13:
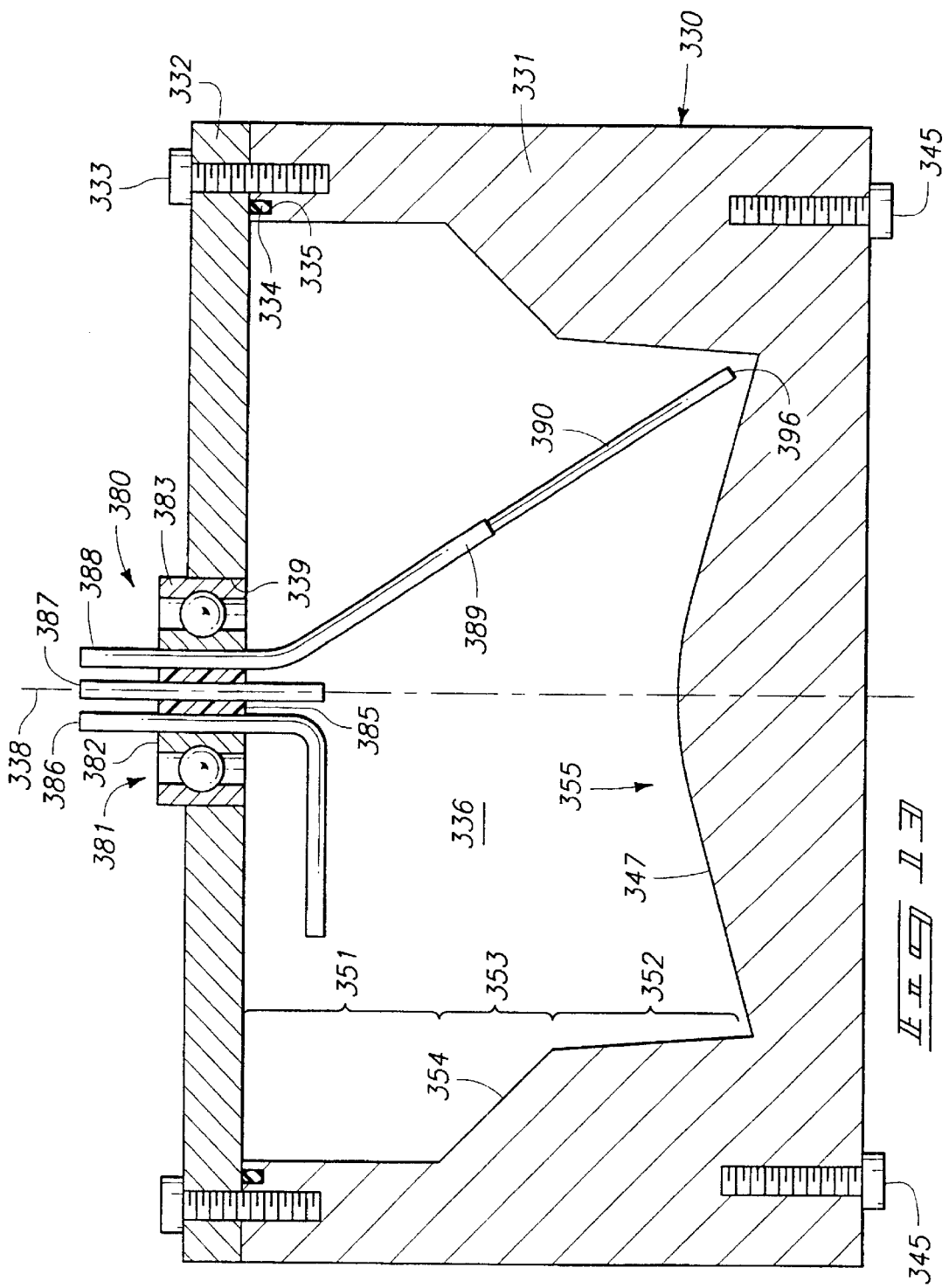
FIG. 13 is a side sectional view of a fourth embodiment centrifuge vessel according to the invention.

FIG. 13 shows a still further embodiment centrifuge vessel 330 made in accordance with the invention. The features of vessel 330 are similar to vessel 30 described in detail hereinabove. Reference numerals in FIG. 13 have been used which are the same as those used in FIGS. 2–6 with the addition of a "3" in the hundreds column. For example the vessel in FIG. 13 is 330 whereas the vessel in FIG. 2 is 30. Similar parts will not be described again for sake of brevity. The following discussion is directed to distinguishing features associated with centrifuge vessel 330 as compared to vessel 30.

The vessel 330 has a domed bottom wall 355 which provides a lower outward trough along the periphery of the second section 352. Separation is performed in a manner substantially similar to that described hereinabove with regard to vessel 30.

Vessel 330 differs from vessel 30 in that the conduit subassembly is provided with a retractable and extendible product outflow conduit 388. Conduit 388 utilizes a first or stationary conduit outer sleeve 389 which extends into and partially downward within the separation chamber. Alternatively, the outer sleeve can be terminated at or near the top plug 385 to minimize interference into the separation chamber 336. The outer sleeve 389 is used as a guide to allow extension and retraction of an extendible conduit part 390. The distal end of extendible conduit 390 is truncated to form a suction port 396 through which one or both fractions of the separated blood are withdraw, in a manner as described above. The extendible and retractable conduit construction of FIG. 13 is desirable in some situations to minimize possible degrading effects of the conduits upon the blood cells. The mechanical action of the swirling fluid against the stationary conduits may cause cell breakdown which in turn may have negative effects upon the products produced by the separator.

Fifth Embodiment Centrifuge Vessel

Figure 14:
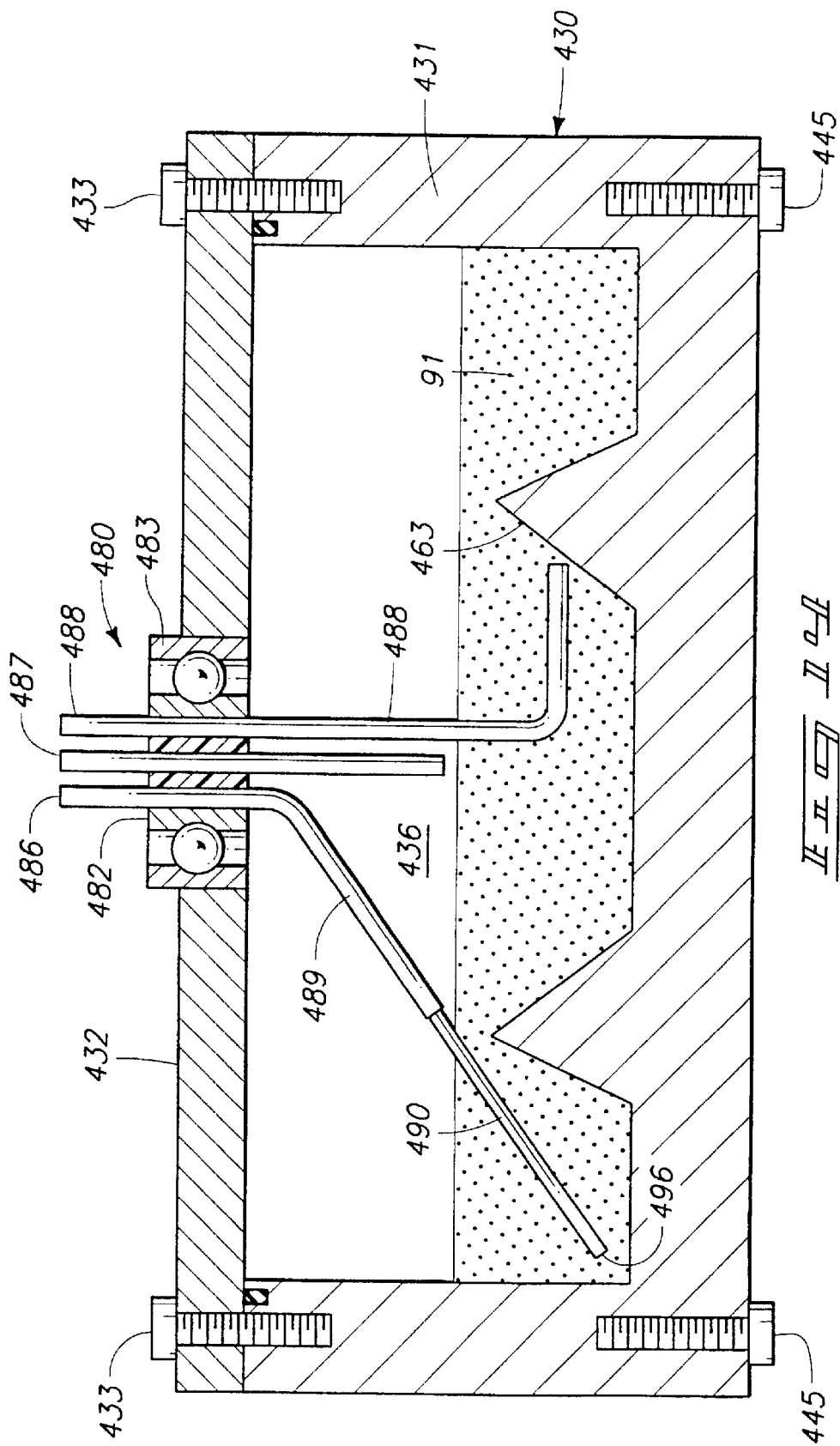
FIG. 14 is a side sectional view of a fifth embodiment centrifuge vessel according to the invention.

FIGS. 14–17 show a still further embodiment centrifuge vessel 430 made in accordance with the invention. The features of vessel 430 are in many respects similar to vessel 30 described in detail hereinabove. Reference numerals in FIG. 13 have been used which are the same as those used in FIGS. 2–6 with the addition of a "4" in the hundreds column. For example the vessel in FIG. 14 is 430 whereas the vessel in FIG. 2 is 30. Similar parts will not be described again for sake of brevity. The following discussion is directed to distinguishing features associated with centrifuge vessel 430 as compared to vessel 30.

Centrifuge vessel 430 is designed to provide radial partitioning of the blood fractions 101 and 102 with the aid of a weir or dam feature 463. The whole blood sample 91 fills lower portions of the separation chamber 436. The chamber is sized so that the weir 463 is below the upper surface of the blood charge when in a nonrotating condition, such as shown in FIG. 14.

Figure 15:
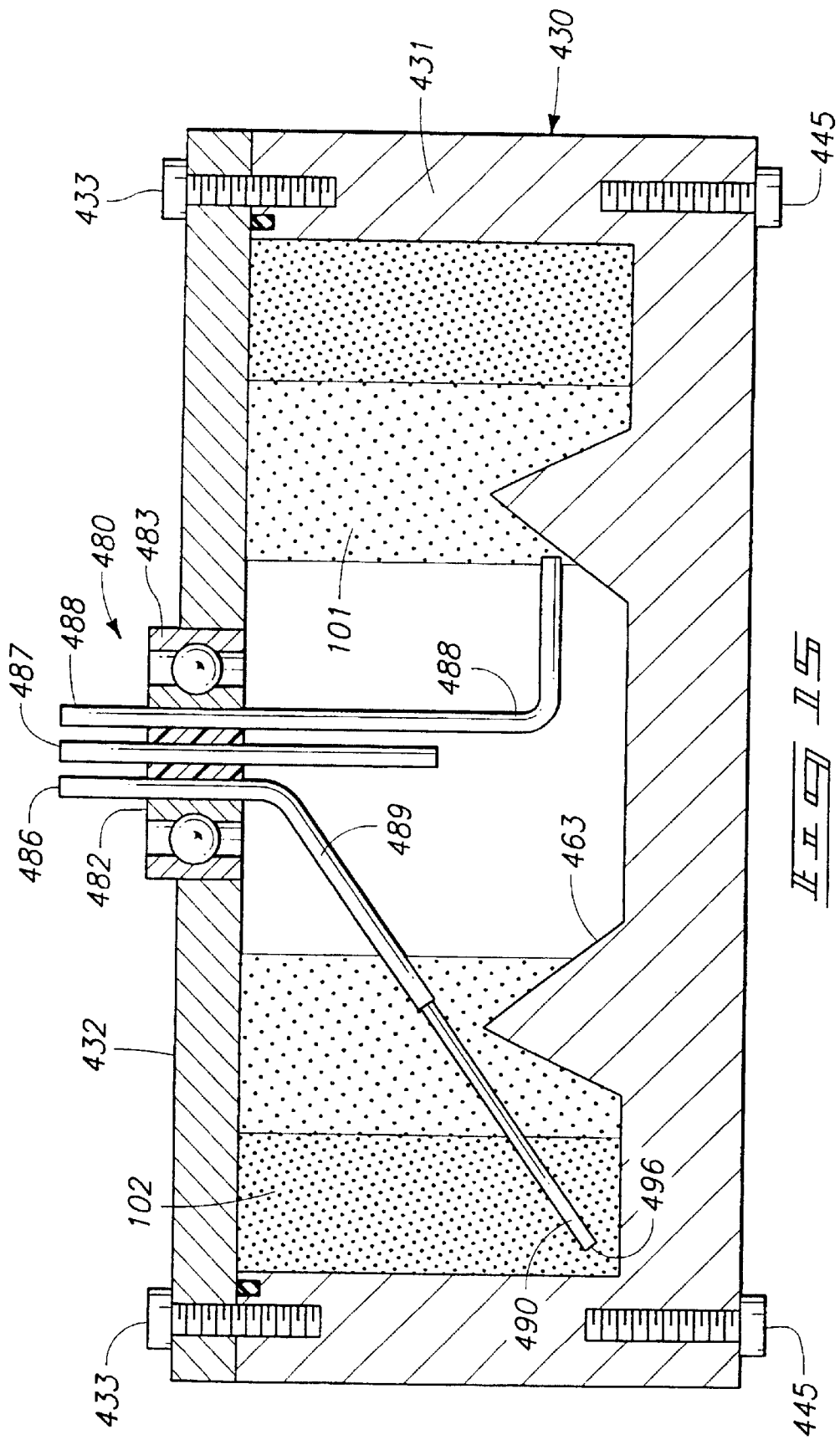
FIG. 15 is a side sectional view similar to FIG. 14 during operation of the blood separator.

FIG. 15 shows the centrifuge vessel 430 after rotation has been started and the outer reaches of the separation chamber are filled by the charge of blood. The blood fractions separate into the light fraction 101 and heavy fraction 102. The heavy fraction 102 is preferably confined totally outside of the weir 463.

Figure 16:
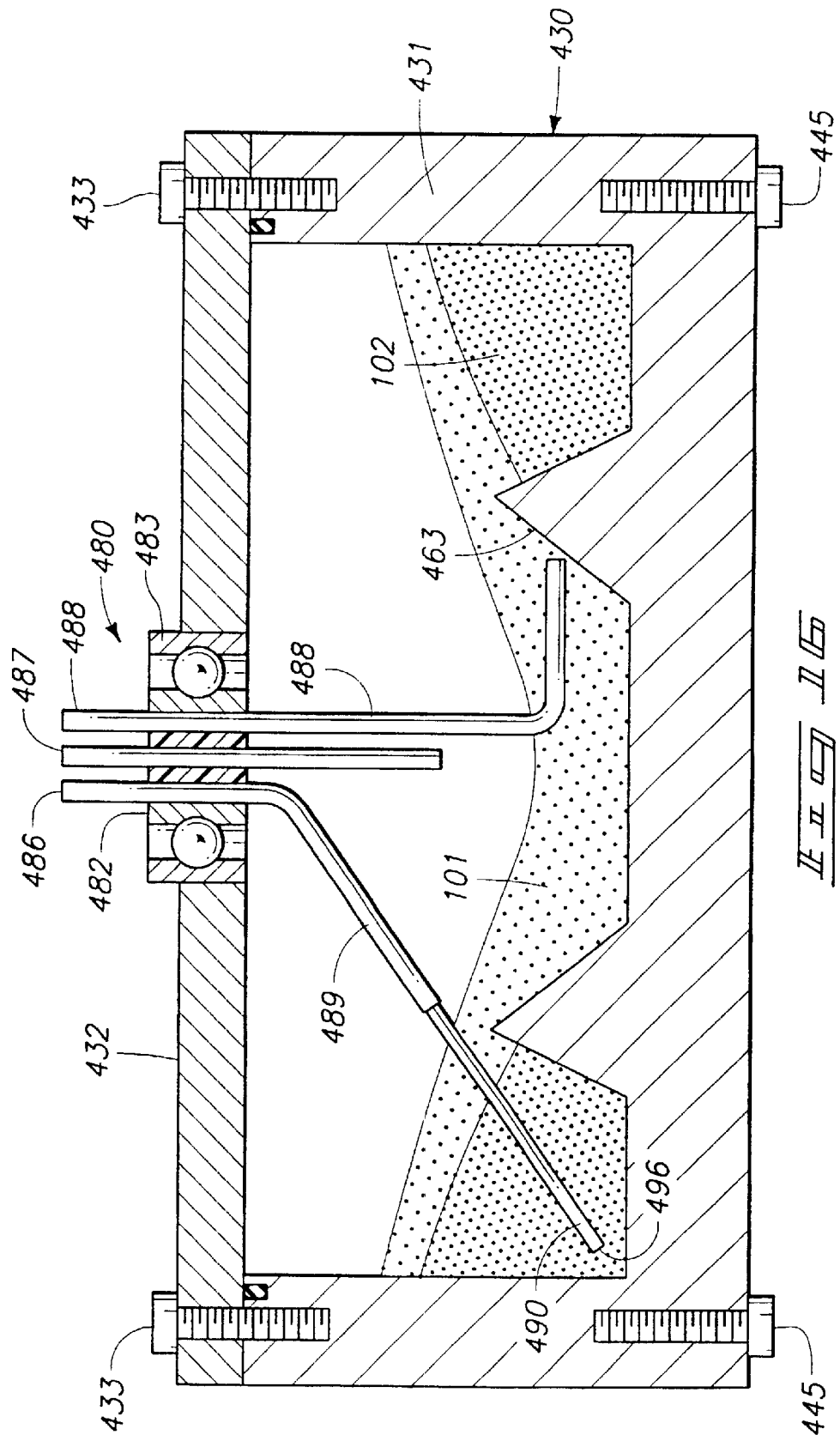
FIG. 16 is a side sectional view similar to FIG. 15 at a subsequent step of processing.
Figure 17:
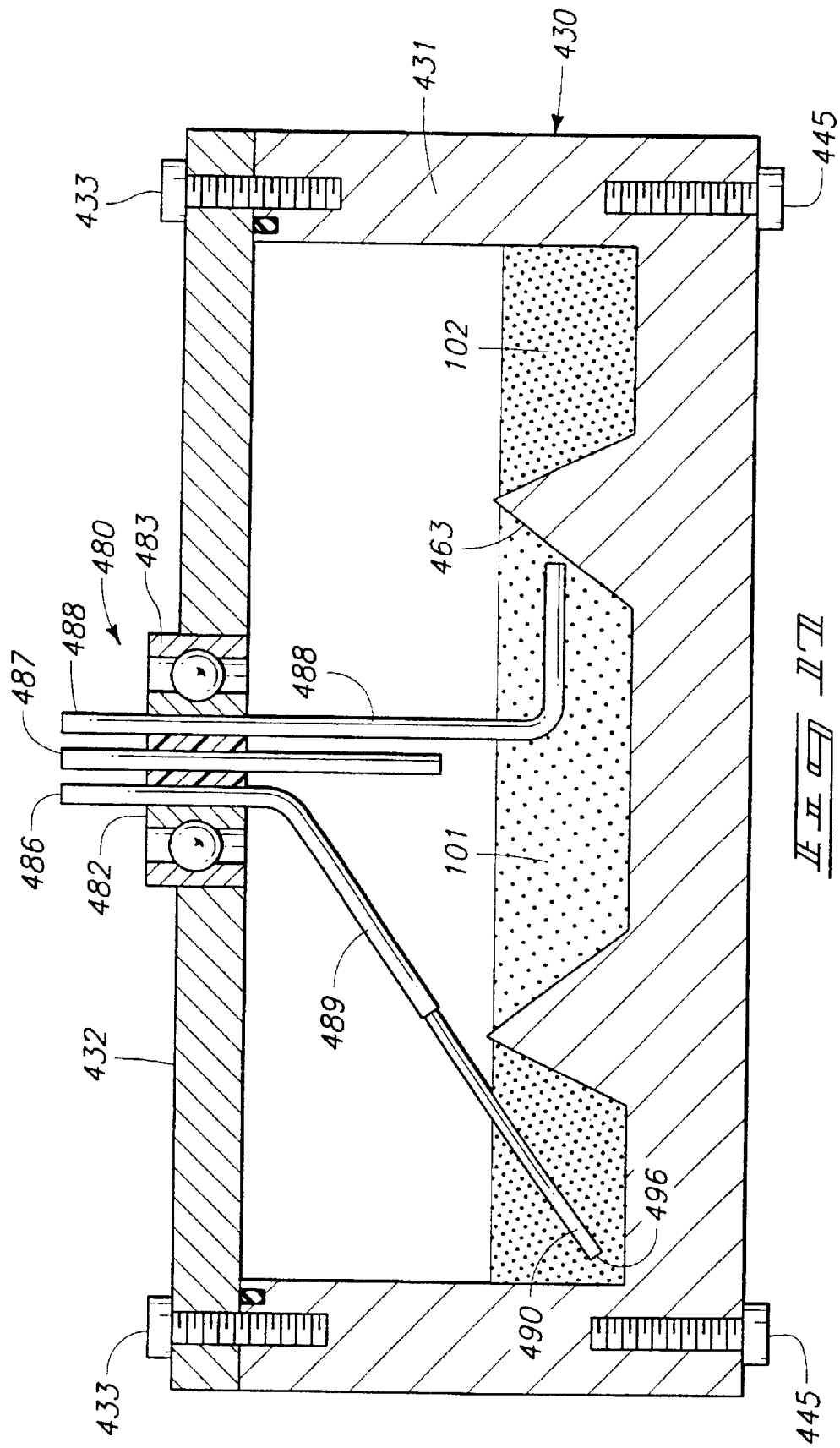
FIG. 17 is a side sectional view similar to FIG. 16 at a subsequent step of processing.

FIG. 16 shows the separation chamber after the rotational speed has been decreased as compared to FIG. 15. The heavy fraction is settling behind the weir. FIG. 17 shows the separated blood sample after centrifugation. The heavy fraction 102 is fully contained outside of the weir. The extendible and retractable product conduit 490 has been extended from the supporting sleeve 489 and the suction port 496 is within the heavy fraction 102. Another product outflow conduit 488 is in position within the light fraction 101 to the inside of weir 463. Both the light and heavy fractions are thus available for withdrawal using a pump or syringe connected to the appropriate conduit.

Methods

The invention further includes novel methods which have in part been described above and will be further described below. The methods according to the invention include a step of charging, supplying or feeding a sample which is to be separated to the separation chamber. The charging or supplying step is preferably accomplished by passing the initial charge 91 through a feed conduit, such as conduit 86. This is advantageously done by pumping the charge therethrough or by otherwise forcing the charge under confinement to reduce the risk or contamination to the operator or area in which the blood separation is being performed. Alternatively, the charging of the separation chamber can be done more simply by natural flow under the force of gravity without pumping or otherwise forcing the fluid into the chamber.

The methods also advantageously include venting the separation chamber as the feeding step is being performed. This minimizes or eliminates any pressure buildup within the separation chamber as the blood charge is being supplied to the separation chamber.

Methods according to the invention also include rotating the centrifuge vessel and enclosed separation chamber. The rotating occurs at a rotational speed sufficient to induce separation of the whole blood charge into desired blood fractions, as explained above. Preferred ranges of rotational speeds are also described above.

The rotating leads after a suitable period of time to a separating action performed upon the blood sample. The separating will in many cases be such as to create a plasma fraction and a blood cell fraction. Other separations may also be possible with adjustments possibly needed in speed, addition of any desired additives, or other processing parameters.

The methods according to the invention also include removing a fraction which has been separated. In some forms of the invention, a single fraction, such as plasma 101, is desired. The fraction can be removed during rotation using some of the embodiments of the invention, for example as shown in FIG. 4 and other FIGS. In other operational situations, it may be more desirable to remove one or more fractions after rotation has stopped, such as shown in FIG. 6 and in other FIGS. Still further it is possible to remove one fraction while rotation is continued, either at full or partial speeds, and then remove a second fraction at reduced or in a nonrotational condition. Still further it may be preferred in some situations to remove a part of a fraction while rotation is occurring and then remove an additional portion or portions while the vessel is nonrotational. The extendable and retractable fluid communication conduits allow such flexibility in removing one or more fractions of the sample while rotating, under partial rotational speeds, or in a nonrotational condition.

The removing of fractions from the separation chamber can be done by sucking the fraction under vacuum pressure, such as by pumping upon one or more of the outflow product conduits. Alternatively, it is possible to force the fractions from the chamber by applying a pressurizes gas to the separation chamber. For example by suppling pressurized gas to a vent conduit and thus causing removal or withdrawal of the fluids through the product conduits. This alternative approach may also necessitate control of flows which may otherwise occur in any other fluid communication conduits present in the system.

Some of the methods according to this invention also include extending a fluid communication conduit between a retracted position and an extended position prior to withdrawing fluids from the separation chamber. The extending step can be done while the vessel is rotating or nonrotating.

Conversely, some of the methods according to this invention also include retracting a fluid communication conduit between an extended position and a retracted position. This may be done either while the vessel is rotating or nonrotating.

The inventive methods also contemplate a step of analyzing the blood fraction output product or products using a variety of possible analytical instruments.

The invention has been described in language more or less specific as to structural and methodical features. It is to be understood, however, that the invention is not limited to the specific features shown and is claimed in its various forms or modifications as is appropriate within the proper scope of the appended claims.

Industrial Applicability

The invention is useful in separating relatively small volume samples of blood or other fluids to provide a separated product or products therefrom.

What is claimed is:

1. A centrifuge for separating a sample into at least two fractions, comprising:
   a frame;
   a centrifuge vessel which is mounted for rotation relative to said frame, said centrifuge vessel having a separation chamber therein which is substantially enclosed;
   at least one conduit which is mounted and arranged so as to allow liquids to be loaded into and removed from the separation chamber while the centrifuge vessel is rotating;
   a driver for rotating the centrifuge vessel;
   a bearing support mounted to the centrifuge vessel supporting the at least one conduit and allowing the at least one conduit to be supported in a position which does not rotate with the centrifuge vessel; and wherein said at least one conduit is mounted in a nonrotating position with portions of the at least one conduit extending into lower outside portions of the separation chamber.

2. A centrifuge for separating a sample into at least two fractions, comprising:

a frame;

a centrifuge vessel which is mounted for rotation relative to said frame, said centrifuge vessel having a separation chamber therein which is substantially enclosed;

at least one conduit which is mounted and arranged so as to allow liquids to be loaded into and removed from the separation chamber while the centrifuge vessel is rotating;

a driver for rotating the centrifuge vessel;

a bearing support mounted to the centrifuge vessel supporting the at least one conduit and allowing the at least one conduit to be supported in a position which does not rotate with the centrifuge vessel; and wherein said at least one conduit includes at least a product conduit and a vent conduit.

3. A centrifuge for separating a sample into at least two fractions, comprising:

a frame;

a centrifuge vessel which is mounted for rotation relative to said frame, said centrifuge vessel having a separation chamber therein which is substantially enclosed;

at least one conduit which is mounted and arranged so as to allow liquids to be loaded into and removed from the separation chamber while the centrifuge vessel is rotating;

a driver for rotating the centrifuge vessel;

a bearing support mounted to the centrifuge vessel supporting the at least one conduit and allowing the at least one conduit to be supported in a position which does not rotate with the centrifuge vessel; and at least one vent which vents the separation chamber to facilitate inflow or outflow of fluids to and from the separation chamber.

4. A centrifuge for separating a sample into at least two fractions, comprising:

a frame;

a centrifuge vessel which is mounted for rotation relative to said frame, said centrifuge vessel having a separation chamber therein which is substantially enclosed;

at least one conduit which is mounted and arranged so as to allow liquids to be loaded into and removed from the separation chamber while the centrifuge vessel is rotating;

a driver for rotating the centrifuge vessel;

a bearing support mounted to the centrifuge vessel supporting the at least one conduit and allowing the at least one conduit to be supported in a position which does not rotate with the centrifuge vessel; and wherein the centrifuge vessel has a first reservoir section and a second reservoir section, the first reservoir section being of a diameter greater than the second reservoir section.

5. A centrifuge for separating a sample into at least two fractions, comprising:

a frame;

a centrifuge vessel which is mounted for rotation relative to said frame, said centrifuge vessel having a separation chamber therein which is substantially enclosed;

at least one conduit which is mounted and arranged so as to allow liquids to be loaded into and removed from the separation chamber while the centrifuge vessel is rotating;

a driver for rotating the centrifuge vessel;

a bearing support mounted to the centrifuge vessel supporting the at least one conduit and allowing the at least one conduit to be supported in a position which does not rotate with the centrifuge vessel; and wherein the centrifuge vessel has a transition slope which is between a first reservoir section and a second reservoir section, the first reservoir section being of a diameter greater than the second reservoir section.

6. A centrifuge for separating a sample into at least two fractions, comprising:

a frame;

a centrifuge vessel which is mounted for rotation relative to said frame, said centrifuge vessel having a separation chamber therein which is substantially enclosed;

at least one conduit which is mounted and arranged so as to allow liquids to be loaded into and removed from the separation chamber while the centrifuge vessel is rotating;

a driver for rotating the centrifuge vessel;

a bearing support mounted to the centrifuge vessel supporting the at least one conduit and allowing the at least one conduit to be supported in a position which does not rotate with the centrifuge vessel; and wherein the centrifuge vessel has a bottom wall which is crowned inwardly to cause liquids to collect along outer portions of the bottom wall.

7. A centrifuge for separating a sample into at least two fractions, comprising:

a frame;

a centrifuge vessel which is mounted for rotation relative to s aid frame, said centrifuge vessel having a separation chamber therein which is substantially enclosed;

at least one conduit which is mounted and arranged so as to allow liquids to be loaded into and removed from the separation chamber while the centrifuge vessel is rotating;

a driver for rotating the centrifuge vessel;

a bearing support mounted to the centrifuge vessel supporting the at least one conduit and allowing the at least one conduit to be supported in a position which does not rotate with the centrifuge vessel; and wherein the centrifuge vessel has a sidewall which includes:

a first reservoir section having a first section diameter which is in the upper portions of the separation chamber;

a second section diameter which is in the lower portions of the separation chamber;

a transition section which is between the first reservoir section and the second reservoir section.

8. A centrifuge for separating a sample into at least two fractions, comprising:

a frame;

a centrifuge vessel which is mounted for rotation relative to said frame, said centrifuge vessel having a separation chamber therein which is substantially enclosed;

at least one conduit which is mounted and arranged so as to allow liquids to be loaded into and removed from the separation chamber while the centrifuge vessel is rotating;

a driver for rotating the centrifuge vessel;

a bearing support mounted to the centrifuge vessel supporting the at least one conduit and allowing the at least one conduit to be supported in a position which does not rotate with the centrifuge vessel; and wherein the centrifuge vessel has a bottom wall which includes a trough portion and a central receptacle which segregates one fraction in the trough portion and another fraction in the central receptacle.

9. A centrifuge for separating a sample into at least two fractions, comprising:

a frame;

a centrifuge vessel which is mounted for rotation relative to said frame, said centrifuge vessel having a separation chamber therein which is substantially enclosed;

at least one conduit which is mounted and arranged so as to allow liquids to be loaded into and removed from the separation chamber while the centrifuge vessel is rotating;

a driver for rotating the centrifuge vessel;

a bearing support mounted to the centrifuge vessel supporting the at least one conduit and allowing the at least one conduit to be supported in a position which does not rotate with the centrifuge vessel; and wherein the centrifuge vessel has a bottom wall which includes:

a central receptacle;

a trough portion outwardly of the central receptacle;

at least one weir dividing the central receptacle and trough portion to segregate one fraction in the trough portion and another fraction in the central receptacle.

10. A centrifuge for separating a sample into at least two fractions, comprising:

a frame;

a centrifuge vessel which is mounted for rotation relative to said frame, said centrifuge vessel having a separation chamber therein which is substantially enclosed; said separation chamber having an upper first reservoir section and a lower second reservoir section, said first reservoir section being of larger diametral size than said second reservoir section;

at least one conduit which is mounted in a non-rotating position from a central upper position and extends downwardly and outwardly within the separation chamber to a position within the lower second reservoir section;

a driver for controllably rotating the centrifuge vessel;

a bearing support mounted to the centrifuge vessel for allowing the at least one conduit to be supported in the non-rotating position relative to the centrifuge vessel.

11. A centrifuge according to claim 10, and further comprising at least one vent which vents the separation chamber to facilitate inflow or outflow of fluids to and from the separation chamber.

12. A centrifuge according to claim 10 wherein the at least one product conduit extends into lower outside portions of the second reservoir section.

13. A centrifuge according to claim 10 wherein the centrifuge vessel has a transition slope which is between the first reservoir section and the second reservoir section.

14. A centrifuge according to claim 10 wherein the centrifuge vessel has a bottom wall which is crowned inwardly to cause liquids to collect along outer portions of the bottom wall.

15. A centrifuge according to claim 10 wherein there are a plurality of conduits forming said at least one conduit.

16. A centrifuge according to claim 10 wherein said at least one conduit includes an extendable portion which has a conduit port within the centrifuge vessel which can be moved into a plurality of positions.

17. A centrifuge according to claim 10 wherein there are a plurality of conduits forming said at least one conduit, and said at least one conduit includes at least one conduit having an extendable portion which has a conduit port within the centrifuge vessel which can be moved into a plurality of positions.

18. A centrifuge according to claim 10 wherein the centrifuge vessel has a bottom wall which is crowned inwardly to cause liquids to collect along outer portions of the bottom wall.

19. A centrifuge according to claim 10 wherein the centrifuge vessel has a bottom wall which includes a trough portion and a central receptacle which segregates one fraction in the trough portion and another fraction in the central receptacle.

20. A centrifuge according to claim 10 wherein the centrifuge vessel has a bottom wall which includes:

a central receptacle;

a trough portion outwardly of the central receptacle;

at least one weir dividing the central receptacle and trough portion to segregate one fraction in the trough portion and another fraction in the central receptacle.

21. A method for separating a fluid sample into at least two fractions, comprising:

placing the fluid sample into a substantially enclosed separation chamber which forms part of a centrifuge vessel;

rotating the centrifuge vessel and separation chamber, said rotating being performed at a rotational speed which causes separation of the at least two fractions;

supporting at least one conduit in a non-rotating position relative to the centrifuge vessel using a bearing mounted upon the centrifuge vessel;

withdrawing a first fraction of said at least two fractions through said at least one conduit supported by said bearing.

22. A method according to claim 21 wherein said withdrawing a first fraction of said at least two fractions through said at least one conduit is performed while said centrifuge vessel is rotating.

23. A method according to claim 21 wherein said placing the fluid sample is done by feeding the fluid sample through said at least one conduit while the centrifuge vessel is rotating.

24. A method according to claim 21 wherein said supporting includes supporting a plurality of conduits using said bearing.

25. A method according to claim 21 and further comprising venting the separation chamber to allow improved feeding and withdrawing of fluid to and from the separation chamber.

26. A method according to claim 21 and further comprising extending an extendable portion of at least one conduit supported by said bearing and having a conduit port within the separation chamber.

27. A method for separating a fluid sample into at least two fractions, comprising:

placing the fluid sample into a substantially enclosed separation chamber which forms part of a centrifuge vessel;

rotating the centrifuge vessel and separation chamber, said rotating being performed at a rotational speed which causes separation of the at least two fractions;

supporting at least one conduit in a non-rotating position relative to the centrifuge vessel using a bearing;

withdrawing a first fraction of said at least two fractions through said at least one conduit while said rotating is being performed;

withdrawing a second fraction of said at least two fractions through said at least one conduit after said rotating has slowed or stopped to allow fluid within the separation chamber to redistribute.

28. A method according to claim 27 wherein said placing the fluid sample is done by feeding the fluid sample through said at least one conduit while the centrifuge vessel is rotating.

29. A method according to claim 27 wherein:

said substantially enclosed separation chamber has an upper first reservoir section and a lower second reservoir section, said first reservoir section being of larger diametral size than said second reservoir section;

said at least one conduit is mounted in a non-rotating position from a central upper position and extends downwardly and outwardly within the separation chamber to a position within the lower second reservoir section to allow said withdrawing a first fraction and said withdrawing a second fraction to occur through the same conduit.

30. A method according to claim 27 wherein said supporting includes supporting a plurality of conduits using said bearing.

31. A method according to claim 27 and further comprising venting the separation chamber to allow improved feeding and withdrawing of fluid to and from the separation chamber.

32. A method according to claim 27 and further comprising extending an extendable portion of at least one conduit supported by said bearing and having a conduit port within the separation chamber.

33. A method for separating a fluid sample into at least two fractions, comprising:

placing the fluid sample into a substantially enclosed separation chamber which forms part of a centrifuge vessel; said substantially enclosed separation chamber having a first reservoir section and a second reservoir section, said first reservoir section being of larger diametral size than said second reservoir section;

rotating the centrifuge vessel and separation chamber, said rotating being performed at a rotational speed which causes separation of the at least two fractions;

withdrawing a first fraction of said at least two fractions through said at least one conduit while said rotating is being performed;

withdrawing a second fraction of said at least two fractions through said at least one conduit after said rotating has slowed or stopped to allow fluid within the separation chamber to redistribute;

said at least one conduit is mounted in a non-rotating position and positioned to allow said withdrawing a first fraction and said withdrawing a second fraction to occur through the same conduit.

34. A method according to claim 33 wherein said placing the fluid sample is done by feeding the fluid sample through said at least one conduit while the centrifuge vessel is rotating.

35. A method according to claim 33 wherein:

said substantially enclosed separation chamber has an upper first reservoir section and a lower second reservoir section;

said at least one conduit is mounted in a non-rotating position from a central upper position and extends downwardly and outwardly within the separation chamber to a position within the lower second reservoir section to allow said withdrawing a first fraction and said withdrawing a second fraction to occur through the same conduit.

36. A method according to claim 33 and further comprising venting the separation chamber to allow improved feeding and withdrawing of fluid to and from the separation chamber.

37. A method according to claim 33 and further comprising extending an extendable portion of at least one conduit having a conduit port within the separation chamber.

38. A method for separating a fluid sample into at least two fractions, comprising:

placing the fluid sample into a substantially enclosed separation chamber which forms part of a centrifuge vessel;

rotating the centrifuge vessel and separation chamber, said rotating being performed at a rotational speed which causes separation of the at least two fractions;

withdrawing a first fraction of said at least two fractions through at least one conduit while said rotating is being performed;

withdrawing a second fraction of said at least two fractions through said at least one conduit after said rotating has slowed or stopped to allow fluid within the separation chamber to redistribute;

said at least one conduit being mounted in a non-rotating position and extending within the separation chamber to allow said withdrawing a first fraction and said withdrawing a second fraction to occur through the same at least one conduit.

39. A method according to claim 38 and further comprising venting the separation chamber to allow improved feeding and withdrawing of fluid to and from the separation chamber.

40. A method according to claim 38 and further comprising extending an extendable portion of at least one conduit supported by said bearing and having a conduit port within the separation chamber.

* * * * *